(12) United States Patent
Zubarev et al.

(10) Patent No.: US 12,140,577 B2
(45) Date of Patent: Nov. 12, 2024

(54) METHOD AND APPARATUS FOR ANALYSING SAMPLES OF BIOMOLECULES USING MASS SPECTROMETRY WITH DATA-INDEPENDENT ACQUISITION

(71) Applicant: Thermo Fisher Scientific (Bremen) GmbH, Bremen (DE)

(72) Inventors: Roman Zubarev, Stockholm (SE); Christian Beusch, Solna (SE)

(73) Assignee: Thermo Fisher Scientific (Bremen) GmbH, Bremen (DE)

( * ) Notice: Subject to any disclaimer, the term of this patent is extended or adjusted under 35 U.S.C. 154(b) by 417 days.

(21) Appl. No.: 17/673,409

(22) Filed: Feb. 16, 2022

(65) Prior Publication Data

US 2022/0260534 A1  Aug. 18, 2022

(30) Foreign Application Priority Data

Feb. 18, 2021  (EP) .................................... 21157833

(51) Int. Cl.
*G01N 30/72* (2006.01)
*G01N 30/14* (2006.01)
(Continued)

(52) U.S. Cl.
CPC ......... *G01N 30/7233* (2013.01); *G01N 30/14* (2013.01); *G01N 33/6851* (2013.01); *G01N 2030/027* (2013.01); *G01N 2570/00* (2013.01)

(58) Field of Classification Search
CPC .... G01N 30/7233; G01N 30/14; G01N 30/02; G01N 30/72; G01N 33/6851;
(Continued)

(56) References Cited

U.S. PATENT DOCUMENTS 9,040,903 B2   5/2015  Coon et al.
10,553,412 B2 * 2/2020  Satulovsky ........ G01N 33/6848
(Continued)

FOREIGN PATENT DOCUMENTS

WO      01/68664 A2    9/2001

OTHER PUBLICATIONS

EP Examination and Search Report mailed on Sep. 15, 2021, to EP Application 21157833.1.
(Continued)

*Primary Examiner* — Suman K Nath
(74) *Attorney, Agent, or Firm* — Thomas F. Cooney

(57) ABSTRACT

A mass spectrometry method comprises: providing a multiplexed sample comprising a mixture of biomolecule-containing samples respectively tagged with mass tags; acquiring MS2 spectra by data-dependent acquisition (DDA) of the multiplexed sample or another mass tagged mixture of the samples during chromatographic elution; acquiring MS2 spectra by data-independent acquisition (DIA) during the elution; forming a spectral library from the DDA MS2 spectra comprising a plurality of the MS2 spectra and the biomolecule retention times; matching fragment-ion peaks in the DIA MS2 spectra to fragment-ion peaks in the MS2 library spectra to find matched biomolecules; determining a total abundance for each matched biomolecule from the DIA MS2 spectra at each of a plurality of retention times; determining abundances of respective reporter ions from the DIA MS2 spectra at the plurality of retention times; and deconvoluting relative abundances of the biomolecules in each respectively tagged biomolecule-containing sample based on the determined abundances.

23 Claims, 10 Drawing Sheets

(51) Int. Cl.
G01N 33/68 (2006.01)
G01N 30/02 (2006.01)

(58) Field of Classification Search
CPC ......... G01N 33/6848; G01N 2030/027; G01N 2570/00; G16B 40/10; H01J 49/0027; H01J 49/004
See application file for complete search history.

(56) References Cited

U.S. PATENT DOCUMENTS

| | | | |
|---|---|---|---|
| 10,768,151 B2* | 9/2020 | Stevens | H01J 49/0036 |
| 2018/0136220 A1 | 5/2018 | Grote et al. | |
| 2021/0333249 A1 | 10/2021 | Remes et al. | |

OTHER PUBLICATIONS

Cheung et al., "Defining the carrier proteome limit for single-cell proteomics" Nature Methods, vol. 18, Jan. 2021, pp. 76-83.
Horn et al., "Automated Reduction and Interpretation of High Resolution Electrospray Mass Spectra of Large Molecules," American Society for Mass Spectrometry, vol. 11, 2000, pp. 320-332.
Itze-Mayrhofer et al. "Quantitative proteomic strategies to study reproduction in farm animals: Female reproductive fluids" Journal of Proteomics, No. 225, 2020, 9 pages.
Jaitly et al. "Decon2LS: An open-source software package for automated processing and visualization of high resolution mass spectrometry data" BMC Bioinformatics, vol. 10, No. 87, 15 pages.
Kong et al. "MSFragger: ultrafast and comprehensive peptide identification in mass spectrometry-based proteomics" Nature Methods, vol. 14, No. 15, May 2017, pp. 513-527.
Macklin et al. "Recent advances in mass spectrometry based clinical proteomics: applications to cancer research," Clinical Proteomics, vol. 17, No. 17, 2020, 25 pages.
Masselon et al. "Identification of tryptic peptides from large databases using multiplexed tandem mass spectrometry: simulations and experimental results" Proteomics, No. 3, 2003, pp. 1279-1286.
Peckner et al. "Specter: linear deconvolution for targeted analysis of data-independent acquisition mass spectrometry proteomics" Nature Methods, vol. 15, No. 5, May 2018, pp. 371-384.
Searle et al. "Chromatogram libraries improve peptide detection and quantification by data independent acquisition mass spectrometry" Nature Communications, vol. 9, No. 5128, 2018, 12 pages.
Stark et al. "Bounded-Variable Least-Squares: an Algorithm and Applications" Technical Report No. 394, Department of Statistics, University of California, Berkeley, Jul. 1993, 37 pages.
Wikipedia, "Tandem Mass Tag" edited on Feb. 2, 2022, 4 pages.
Teleman et al. "Dinosaur: A Refined Open-Source Peptide MS Feature Detector" Journal of Proteome Research, vol. 15, 2016, pp. 2143-2151.
Thompson et al. "Tandem Mass Tags: A Novel Quantification Strategy for Comparative Analysis of Complex Protein Mixtures by MS/MS" Analytical Chemistry, vol. 75, No. 8, Apr. 15, 2003, pp. 1895-1904.
Tian et al. "A Versatile Isobaric Tag Enables Proteome Quantification in Data-Dependent and Data-Independent Acquisition Modes" Analytical Chemistry, vol. 92, 2020, pp. 16149-16157.
Yuan et al. "Features-Based Deisotoping Method for Tandem Mass Spectra" Advances in Bioinformatics, 2011, 13 pages.

* cited by examiner

METHOD AND APPARATUS FOR ANALYSING SAMPLES OF BIOMOLECULES USING MASS SPECTROMETRY WITH DATA-INDEPENDENT ACQUISITION

CROSS-REFERENCE TO RELATED APPLICATION

The present application claims, under 35 U.S.C. § 119(a), priority to and the benefit of the filing date of European Application EP21157833.1, filed on Feb. 18, 2021, the disclosure of which is hereby incorporated herein in its entirety.

FIELD

The present disclosure relates to the field of mass spectrometry. Aspects of the disclosure relate to the quantitation of biomolecules using mass spectrometry, particularly but not exclusively biomolecules such as peptides and proteins. The disclosure is applicable to the field of mass spectrometry based proteomics.

BACKGROUND

Data-independent acquisition (DIA) is an analysis mode in mass spectrometry, in particular in MS-based proteomics. In DIA, all precursor ion species within a specific m/z range are selected and fragmented to generate fragment ions (also termed product ions). The fragment ions are then mass analysed in an MS/MS (also termed MS2) scan, which results in a complex MS2 mass spectrum due to co-fragmentation of precursor ions. Attempts have been made to deconvolute the co-fragmentation, such as described in Peckner et al, Specter: linear deconvolution for targeted analysis of data-independent acquisition mass spectrometry proteomics, *Nature methods* vol. 15, no. 5 (2018), 371. The main advantage of DIA, however, is the low number of "missing" peaks, which are a significant problem in the alternative method for MS2 analysis, data-dependent acquisition (DDA), due to the stochastic nature of precursor selection in DDA. The DDA method utilises data acquired in an MS1 (precursor ion) scan to select, based on predetermined criteria, one or more specific ion species for fragmentation and subsequent MS2 analysis. This results in a simpler, more specific MS2 mass spectrum due to the narrower m/z range used to select the specific precursor ions but at the expense of not selecting every precursor. The predetermined criteria for selecting the ion species from the MS1 analysis in DDA may comprise one or more of: peak intensity, charge state (z), mass-to-charge ratio (m/z), peak inclusion/exclusion lists, or isotopic pattern.

The low number of "missing values" that accompanies DIA is of particular importance when an experiment encompasses a large number of independent samples, with the task to compare proteins abundances between the samples. As an example, if 100 samples need to be compared with 1% of missing values in each sample randomly distributed among the detected proteins, then on average $0.99^{100}=0.366$ of all proteins, or 36.6%, will be quantified in all samples. In contrast, with 0.5% missing values, >60% of all proteins will be quantified in all samples. The problem is particularly severe in single cell proteomics (SCP), in which a large number of samples (for example ≥100, or ≥1000) need to be compared with each other.

A recent development in the field of MS-based proteomics has been the use of mass tags (also termed mass labels) that are cleavably attached to an associated molecule of interest. The so-called isobaric tags are used for the identification and quantification of biological macromolecules, such as proteins, peptides, nucleic acids, and nucleotides for example. The particular approach of using tandem mass tag (TMT) labelling is described, for example, in WO 01/68664 A2 and Thompson et al Anal. Chem. 2003, 75, 1895-1904. TMTs contain four regions or moieties, namely a mass reporter region or moiety (M), a cleavable linker region or moiety (F), a mass normalization region or moiety (N) and a protein reactive group (R). The chemical structures of all the tags (also termed channels) in a TMT set are identical but each contains isotopes substituted at various positions, such that the mass reporter and mass normalization regions have different molecular masses in each tag. However, the combined M-F-N-R regions of the tags have the same total molecular weights and structure so that during chromatographic or electrophoretic separation and in single MS mode, molecules labelled with different tags are indistinguishable. Upon fragmentation in MS/MS (MS2) mode, sequence information is obtained from fragmentation of the peptide back bone and quantification data are simultaneously obtained from fragmentation of the tags, giving rise to mass reporter ions (see https://en.wikipediorg/w/index.php?title=Tandem_mass_tag&oldid=882091680).

In a typical bottom-up proteomics workflow, protein samples are enzymatically digested to produce peptides. Each digested sample is derivatized or labelled with a different isotopic variant of the tag from a set of isobaric tags. The labelled samples are then mixed, typically in equal ratios, and analyzed simultaneously in one liquid chromatography-MS (LC-MS) experimental run. Since the tags are isobaric and have identical chemical properties, the isotopic variants appear as a single composite peak at the same m/z value in an MS1 (precursor) scan with identical liquid chromatography (LC) retention times. During MS2 scans in the LC-MS analysis, the fragmented peptides produce sequence-specific fragment ions (also termed product ions). The fragment ions are used to determine the peptide sequence and the relative abundances of the reporter ions of the tags reflect the relative ratio of the peptide in the individual samples that were combined. The MS2 scan is therefore required to detect the reporter ions of the tags. A key benefit of isobaric labeling, such as TMT labelling, over other quantification techniques is the multiplex capabilities and associated increased throughput. The ability to combine and analyze several samples simultaneously in one LC-MS run eliminates the need to analyze multiple data sets and eliminates run-to-run variation.

In the case of DIA MS analysis, a problem arises with multiplexing, for example, in the use of TMT labeling, due to the overlap of the TMT reporter ion signals from different (peptide) precursors that are simultaneously fragmented due to the wide (e.g. 10-20 m/z units (Th)) MS2 mass selection window typically used in DIA. FIG. 1 illustrates this schematically with an example of a 6-plex TMT multiplexed sample. In the upper plot, the abundance (I) of several peptides as a function of chromatographic retention time (RT) is shown. Three peptides, denoted 1, 2 and 3, are shown having overlapping elution peaks, including at time to. In the middle plot is shown the MS1 (precursor ion) mass spectrum at time to. The peak positions for the co-eluting peptides 1, 2, 3 are shown among the peaks for several other co-eluting peptides (not shown in the upper plot). The m/z values for peptides 1, 2, 3 are close together so that the three peptide precursors are selected in the same mass isolation window for the DIA MS2 scan, which is shown in the lower plot.

Accordingly, the MS2 spectrum is chimeric in containing peaks of fragment ions from the three precursors. In addition to the peaks of the unfragmented precursor ions shown at the right side of the spectrum, the fragments from peptide 1 are also denoted 1, fragments from peptide 2 are denoted 2 and fragments from peptide 3 are denoted 3. The intensities (I) of the reporter ions, used for quantitation of peptides in the individual samples, are shown on the left side (low m/z) of the spectrum. The peak of one reporter ion is shown expanded below the spectrum and the contribution to the single peak intensity from the three peptides is indicated. Thus, the relative abundances of the individual peptides in the samples cannot be deduced from the single reporter ion peaks representing each sample.

In contrast, in DDA analysis, the MS2 selection window can be 0.8 m/z units or narrower, which in practice alleviates the overlap problem and allows for sample multiplexing. Thus, DDA can analyze 10-16 TMT-multiplexed samples. However, as described above, this increase in throughput is achieved in DDA at the expense of an increased number of missing values in the MS2 spectrum.

It would, therefore, be advantageous to be able to utilise DIA for multiplexed isobaric labeled samples (TMT tagged samples) to allow both the high throughput of TMT workflows and the low number of missing mass spectral data inherent with DIA, whilst addressing the problem of overlap of reporter ion signals from different precursors. Against the above background the present disclosure has been made.

SUMMARY

The present disclosure provides a method of mass spectrometry according to the appended claims.

The present disclosure in one aspect provides a method of mass spectrometry for analysing samples of biomolecules, comprising:
providing a multiplexed sample comprising a mixture of biomolecule-containing samples, wherein the biomolecule-containing samples are respectively tagged with mass tags;
acquiring MS2 spectra by data-dependent acquisition (DDA) of the multiplexed sample or another mass tagged mixture of the biomolecule-containing samples as it elutes from a liquid chromatographic device;
acquiring MS2 spectra by data-independent acquisition (DIA) of the multiplexed sample as it elutes from the liquid chromatographic device;
forming a spectral library from the MS2 spectra acquired by DDA comprising a plurality of MS2 spectra representing a plurality of mass-tagged molecular ions of biomolecules and their fragment ions and the retention times (i.e. elution times) of the biomolecules;
matching peaks of fragment ions in the MS2 spectra acquired by DIA to peaks of fragment ions in the MS2 spectra of the spectral library to find matched biomolecules;
determining a total abundance for all mass tags for each matched biomolecule from the MS2 spectra acquired by DIA at each of a plurality of retention times (i.e. retention times across the elution of the multiplexed sample), preferably by summing intensities of peaks of fragment ions and molecular ions of the matched biomolecule in MS2 spectra acquired by DIA;
determining abundance of respective reporter ions derived from the mass tags from the MS2 spectra acquired by DIA at the plurality of retention times; and
deconvoluting relative abundances of the biomolecules in each biomolecule-containing sample based on the determined abundances of the respective reporter ions and the determined total abundances for all mass tags of the matched biomolecules at corresponding retention times over the plurality of retention times.

In preferred embodiments, the biomolecules are peptides, preferably peptides produced by digesting proteins.

In preferred embodiments, the biomolecule-containing samples are samples of digested single cell proteomes.

In preferred embodiments, the mass tags are tandem mass tags (TMTs).

In preferred embodiments, forming the spectral library includes processing the MS2 spectra acquired by DDA, comprising one or more of the following:
(i) removing peaks representing ions that are not specific to a biomolecule;
(ii) deisotoping the spectra;
(iii) binning peaks of fragment ions of the biomolecules into a plurality of m/z bins and keeping the most intense peak in each bin;
(iv) removing duplicate spectra.

In preferred embodiments, the spectral library comprises mass spectra for both identified and unidentified biomolecules.

In preferred embodiments, the mass spectra in the spectral library for identified biomolecules are obtained by finding peaks in MS1 spectra acquired by the data-dependent acquisition (DDA), finding peaks of fragment ions in the MS2 spectra acquired by DDA that correlate with the peaks in the MS1 spectra, and identifying structures of the biomolecules based on the peaks in MS1 and the correlating peaks of fragment ions.

In preferred embodiments, finding peaks in the MS1 spectra comprises identifying isotopic clusters in the MS1 spectra that are expected to belong to biomolecules.

In preferred embodiments, the mass spectra in the spectral library for the identified biomolecules comprise only correlating peaks of fragment ions that are supported by the identified structures.

In preferred embodiments, correlating fragment ions that are not supported by the identified structures of the biomolecules are used to represent unidentified biomolecules in the spectral library.

In preferred embodiments, the unidentified biomolecules comprise peptides derived from the dark proteome (dark proteome peptides).

In preferred embodiments, in the matching step, mass spectra in the spectral library are each matched against the mass spectra acquired by DIA in a retention time window around the retention time of the library mass spectra.

In preferred embodiments, the method further comprises calculating for each mass spectra in the spectral library a series of probability scores at each time point in the retention time window and removing a number of spectra from the matching based on the series of probability scores.

In preferred embodiments, the series of probability scores comprises a spectra matching score, a sum-intensity of all matched fragment ions and/or the number of matched fragment ions.

In preferred embodiments, summing intensities of peaks of fragment ions and, optionally, molecular ions to determine an abundance for each biomolecule comprises calculating a sum of intensities of matched peaks of fragment ions in the MS2 spectra acquired by DIA in a retention time interval.

In preferred embodiments, the apex of the elution of each biomolecule is determined and a predetermined number of the MS2 spectra acquired by DIA either side of the apex are used to determine the retention time interval.

In preferred embodiments, the method further comprises fitting a peak shape model, preferably a Gaussian model, for the intensity of each matched fragment ion through the time points in the retention time interval, and fragment ions with a correlation below a threshold for the model are removed.

In preferred embodiments, the method further comprises calculating a median intensity of all matched peaks of fragment ions in the MS2 spectra acquired by DIA, and correlating each fragment ion intensity against the median, wherein fragment ions not having a correlation above a threshold are removed.

In preferred embodiments, deconvoluting the relative abundances of the biomolecules from abundances of the reporter ions comprises using a set of linear equations. Each linear equation of the set is preferably constructed for a (different) respective retention time, i.e. for a different MS2 spectrum.

In preferred embodiments, each linear equation relates an abundance of a reporter ion of one of the biomolecule-containing samples to a linear combination of abundances of each of the biomolecules in that biomolecule-containing sample, wherein the abundance of each biomolecule in that sample is expressed as the total abundance of that biomolecule for all mass tags, i.e. in all the biomolecule-containing samples, multiplied by the relative abundance of the biomolecule in that biomolecule-containing sample.

In preferred embodiments, each linear equation relates the determined abundances of the respective reporter ions to a linear combination of the abundances of the biomolecules in each of the biomolecule-containing samples at a respective retention time, wherein the abundance of each biomolecule in each of the samples is expressed as the determined total abundance of the biomolecule multiplied by the relative abundance of the biomolecule in the sample Preferably, a set of M linear equations is constructed for N matched biomolecules in the samples (N typically <10,000) where M≥N*X, wherein X is the number of MS2 scans (for a specific DIA window) or the number of respective reporter ions. Preferably, the total number of DIA MS2 scans acquired is M, or at least M. In preferred embodiments, deconvoluting the relative abundances of the biomolecules from the abundances of the reporter ions comprises solving matrices, for example to solve the linear equations. In preferred embodiments, the deconvoluting comprises constructing matrices, wherein a first matrix (M1) comprises the determined abundances of the respective reporter ions as columns with the retention times corresponding to the rows and a second matrix (M2) comprises the determined total abundances of the (respective) matched biomolecules as columns with the retention times corresponding to the rows. A third matrix (M3) can comprise the relative abundances of the biomolecules in each biomolecule-containing sample. The third matrix can comprise the relative abundances of the biomolecules in each biomolecule-containing sample as columns with the (respective) biomolecules corresponding to the rows. The relative abundances of the biomolecules in each biomolecule-containing sample can be found from solving the formula M1=M2*M3.

In some embodiments, one of the biomolecule-containing samples is a pooled sample of the other samples and deconvoluting the abundances of the reporter ions comprises, within an elution or retention time for each biomolecule based on the determined abundances of the biomolecules, fitting a linear function that correlates the abundance of an individual reporter ion and the abundance of a reporter ion of the pooled sample.

Another aspect of the disclosure provides a mass spectrometer under the control of a controller, wherein the controller is configured such that the mass spectrometer is operable to perform the steps of the method according to the present disclosure. In particular, the disclosure provides a mass spectrometer for analysing samples of biomolecules, comprising: an ionization source for producing precursor ions of the biomolecules provided by a chromatographic device; a mass selector for selecting a mass range of the precursor ions; a fragmentation device for fragmenting precursor ions selected by the mass selector to produce fragment ions; a mass analyser for performing mass analysis of the precursor and fragment ions; and a controller configured to cause the mass spectrometer to perform the method of mass spectrometry according to the method of the disclosure.

Another aspect of the disclosure provides a computer program which, when executed by one or more processors of a computer, causes the one or more processors to carry out a method according to the disclosure, generally by controlling the mass spectrometer to perform the method of mass spectrometry according to the disclosure herein. The computer is, accordingly, preferably part of the controller of the mass spectrometer. The computer program may be stored on a computer-readable medium for execution by the processors, for example stored on a flash drive, hard disk drive etc. Thus, the disclosure also provides a computer readable medium having stored thereon a computer program which, when executed by one or more processors of a computer, causes the one or more processors to control a mass spectrometer to perform the method of mass spectrometry according to the method of the disclosure.

This disclosure will be mainly illustrated hereafter using the example of peptides as the biomolecules, for example peptides which have been derived from proteins. However, the disclosure is not limited to peptides and may be utilised with other biomolecules. The term biomolecules herein therefore encompasses, for example, peptides, proteins, nucleic acids, nucleotides and other such biomolecules. The disclosure may, in particular, be extended to analysis of biomolecules selected from: biopolymers, proteins, peptides, polypeptides, amino acids, carbohydrates, sugars, fatty acids, lipids, vitamins, hormones, polysaccharides, phosphorylated peptides, phosphorylated proteins, glycopeptides, glycoproteins, polynucleotides, oligionucleotides, polynucleosides, oligionucleosides, DNA, fragments of DNA, cDNA, fragments of cDNA, RNA, fragments of RNA, mRNA, fragments of mRNA, tRNA, fragments of tRNA, monoclonal antibodies, polyclonal antibodies, ribonucleases, enzymes, metabolites, and/or steroids. The samples analysed may comprise at least: 2, 5, 10, 20, 50, 100, 500, 1000, 5000 or 10,000 different biomolecules.

DETAILED DESCRIPTION

Various embodiments according to the present disclosure will now be described with reference to the accompanying figures. The embodiments are intended to illustrate various features and are not intended to be limiting on the scope of the disclosure. It will be appreciated that variations to the embodiments can be made while still falling within the scope of the appended claims.

Figure 1:
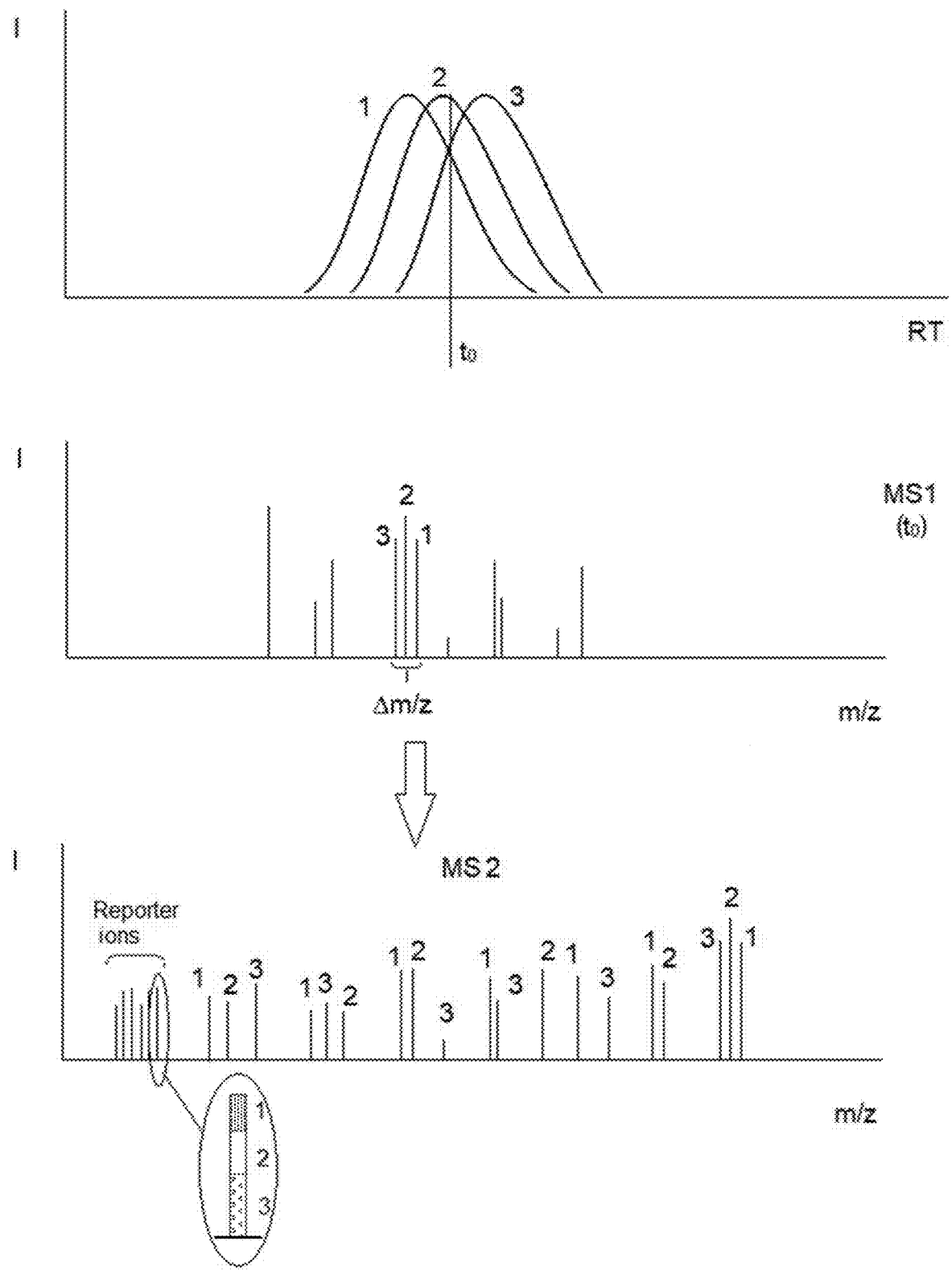
FIG. 1 shows a schematic example of a chromatogram (upper plot), MS1 spectrum (middle plot) and MS2 spectrum (lower plot) for co-eluting TMT tagged peptides.
Figure 2:
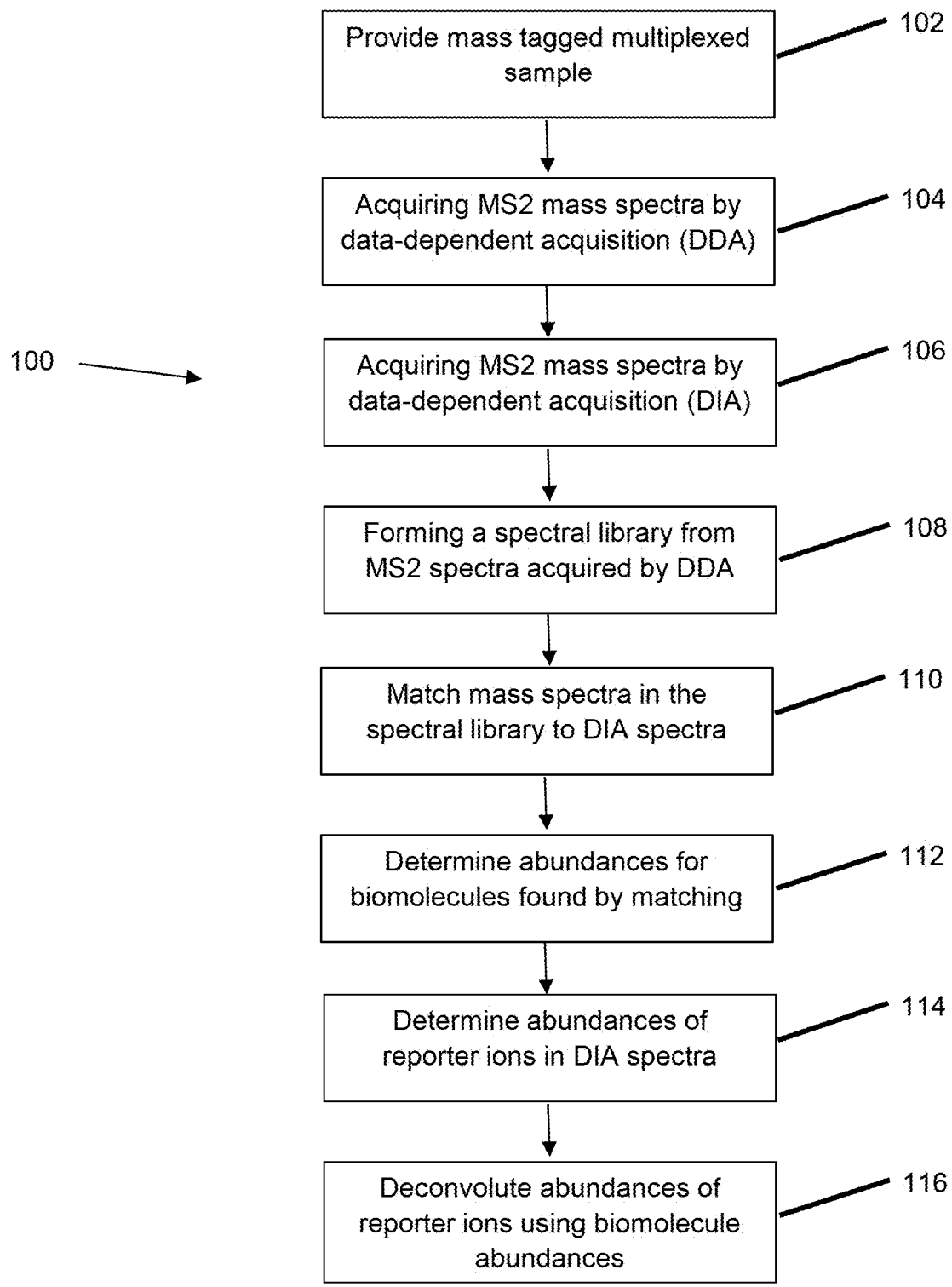
FIG. 2 shows a flow diagram of a method in accordance with the present disclosure.

An embodiment of the disclosure relates to mass spectrometry for analysing samples of biomolecules. The disclosure provides a method of mass spectrometry for analysis of biological samples and particularly of biomolecules, comprising analysing a multiplexed sample comprising a mixture of (individual) samples containing biomolecules, wherein the samples have been respectively mass tagged. FIG. 2 illustrates a flow diagram of a method 100 in accordance with the present disclosure. In step 102 a mass tagged multiplexed sample is provided. In more detail, the method comprises a step of providing a multiplexed sample comprising a mixture of biomolecule-containing samples, wherein in the multiplexed sample the samples have been respectively mass tagged with individual (i.e. unique/different) mass tags. The individual samples containing biomolecules are preferably respectively labelled with a different isobaric mass tag from a set of isobaric mass tags. This means that each biomolecule in the same sample is mass tagged with the same mass tag. When fragmented and analysed using MS2 mass scans as described below, each biomolecule from the same sample yields the same (unique) reporter ion. The mass tagged samples can then be mixed to form the multiplexed sample. The mass tagged samples are typically mixed in equal ratios to form the multiplexed sample. The biomolecules will be illustrated as peptides in most of the description hereafter but, as mentioned above, the disclosure is not limited to peptides. References to peptides hereafter can therefore be understood as including references to other biomolecules as appropriate (nucleic acids, nucleotides (polynucleotides and oligonucleotides)).

Each biomolecule-containing sample contains a plurality of different biomolecules. The identities of the biomolecules can be substantially the same in each biomolecule-containing sample but their abundances can differ. Often, the biomolecule-containing samples have more than 90%, 95%, 99%, 99.5%, or 99.9% of their biomolecules in common. This is typically the case for samples in single cell proteomics experiments, in which the peptides are the same for all of the single cell proteomes, but the abundances are different.

The mass tags may be tandem mass tags (TMTs). The set of isobaric mass tags may have X number of mass tags in the set, e.g. X=2, 3, 4, 5, 6, 7, 8, 9, 10, 11, 12, 13, 14, 15, 16, 17, 18, 19, or 20, and so on; X is commonly 2 to 16, or 2 to 11, or 2 to 10 for commercially available mass tag sets, e.g. X may be 2, 3, 4, 5, 6, 7, 8, 9, 10, 11, 12, 13, 14, 15 or 16). Accordingly, the number of individual samples that are tagged and mixed can be 2, 3, 4, 5, 6, 7, 8, 9, 10, 11, 12, 13, 14, 15, 16, 17, 18, 19, or 20, and so on but is typically in the range 2 to 16, or 2 to 10.

The samples of biomolecules are typically samples of peptides. The samples of peptides are typically provided by a bottom-up proteomics workflow, wherein protein samples are enzymatically digested to produce the samples of peptides. Each individual (digested) sample is preferably tagged or labelled with a different isotopic variant of the mass tag from the set of isobaric tags. The mass tagged samples are then mixed, typically in equal ratios, to form the multiplexed sample. The multiplexed sample is then analyzed using liquid chromatography-MS (LC-MS) as described below.

In some embodiments of the method described herein, in a multiplexed sample prepared using a set of X mass tags and comprising X samples, the samples are individual peptide samples, typically formed from digestion of individual protein samples. The disclosure has application, for example, in embodiments where the individual protein samples constitute proteomes from single cells (each protein sample is the proteome from a single cell).

In some other embodiments of the method described herein, also suited to single cell proteomics analysis, in a multiplexed sample prepared using a set of X mass tags, a number of samples 1 to (X−1) in the multiplexed sample are individual peptide samples formed from digestion of individual protein samples and the $X^{th}$ sample in the multiplexed sample is a pool of the individual samples 1 to (X−1). The $X^{th}$ (pooled) sample can be used for normalization of the other samples. The individual peptide samples can be digests of single cell proteomes. In the case of single cell proteomes, the $X^{th}$ (pooled) sample, also termed the 'carrier proteome' or 'bulk channel', can be diluted to an equivalent of N cells (N can be 1 to 500 or more, but more preferably N is 5 to 200, 5 to 100, or 5 to 50. It has been reported that a recommended value is N~20 (Cheung, T. K. et al. "Defining the carrier proteome limit for single-cell proteomics." *Nature Methods*, vol. 18 (2020), 76-83). In some embodiments N≥X). For example, in a TMT-10 (i.e. 10-plex set of TMTs) multiplexed sample, 9 of the TMT channels can represent individual samples, such as single cell proteomes, and the $10^{th}$ channel can represent a pooled sample of the other 9 samples, thus reflecting the bulk proteome. The $10^{th}$ TMT channel can be used for normalisation of the other 9 channels and can be prepared as or diluted to an equivalent of N cells (e.g. N≥20, in particular N~20 as described above, or N≥10).

The multiplexed sample is analyzed using liquid chromatography-MS (LC-MS). Since the tags are isobaric and have identical chemical properties, a particular peptide tagged with the isotopic variants in the multiplexed sample appears as a single composite peak at the same m/z value in an MS1 (precursor) scan with identical liquid chromatography retention time (RT). During MS2 (i.e. MS/MS) scans in the LC-MS analysis, the fragmented peptides produce structure-specific fragment ions (also termed product ions). The fragment ions are used to determine the peptide sequence and the relative abundances of the reporter ions of the mass tags reflect the relative abundances (ratio) of the peptide in the individual samples that were combined. The MS2 scan is therefore required to detect the reporter ions of the tags.

As a chromatographic peak of a particular peptide elutes (from the chromatographic device/column) with time, the abundances in the MS2 analysis of both the reporter ions originating from the peptide as well as its structure-specific fragment ions start to change proportionally to the peptide abundance. For each given reporter ion (mass tag channel), this proportionality or proportionality coefficient depends upon the relative abundance of the eluting peptide in the particular (individual) sample labelled with the given mass tag, i.e. relative to its abundance in the other labeled samples. This can be utilised in this disclosure to extract the individual relative abundance of the peptide in the particular (individual) sample (i.e. compared to the abundances in the other samples). In DIA, however, a problem arises with multiplexing samples due to the overlap of the reporter ion signals from different (peptide) precursors due to the wide (e.g. 10-20 m/z units (Th)) MS2 mass selection window typically used in DIA. The present disclosure addresses the deconvolution of reporter ion signals from different, co-fragmented (peptide) precursors in mass spectrometry data obtained from DIA.

The LC-MS analysis preferably comprises acquiring MS2 mass spectra of the peptide-containing samples using data-dependent acquisition (DDA), typically prior to the DIA analysis, as shown in step 104 of FIG. 2. This DDA analysis can comprise acquiring MS2 mass spectra by DDA of the multiplexed sample. Alternatively to performing the DDA on the multiplexed sample of respectively tagged individual samples, the DDA analysis may comprise acquiring MS2 mass spectra using data-dependent acquisition (DDA) of another mixture of the peptide-containing samples. Such other mixture is also mass tagged, preferably with an isobaric mass tag (TMT), so that the peptides in that mixture have the same retention time as they do in the multiplexed sample. The other mixture, when used, preferably comprises the same ratio of peptide-containing samples as the multiplexed sample (e.g. equal ratios of each peptide-containing sample). In some embodiments, the other mixture may be tagged differently to the multiplexed sample, for example it may be tagged with a single mass tag, rather than comprise the respective mass tags of the multiplexed sample. The mass tag or tags of the other mixture, however, is or are from the same isobaric set of mass tags as the mass tags of the multiplexed sample. For example, the other mixture can be a pooled sample of the other samples, optionally comprising a higher concentration of the biomolecules (than the multiplexed sample) to provide higher intensity peaks in the mass spectra, which is useful for forming the spectral library. For example, the other mixture can be the $X^{th}$ (pooled) sample in some of the embodiments described herein.

The MS2 mass spectra acquired by DDA can be used to provide a spectral library or database. The LC-MS analysis thus can comprise eluting the (tagged) multiplexed sample (typically a portion thereof), or the other (tagged) mixture of the peptide containing samples, from a liquid chromatographic device, such as a chromatographic column, and acquiring MS2 mass spectra by performing data dependent acquisition (DDA) of the multiplexed sample or other mixture as it elutes from the liquid chromatographic device. In embodiments that utilise a pooled sample of the individual samples, the DDA analysis can be performed on the pooled sample.

The DDA comprises multiple (repeated) cycles of analysis as the sample elutes. Each DDA cycle comprises a set of: an MS1 (precursor ion) scan followed by a plurality of (data-dependent) MS2 scans. The retention times (RT) are preferably recorded of each of the MS1 and MS2 scans. The MS1 scan covers the mass range of interest of the peptides in the sample. The data acquired in the MS1 scan is used to select one or more specific ion species for fragmentation and the subsequent MS2 analysis. Predetermined criteria that can be used for selecting the ion species from the MS1 analysis may comprise one or more of: peak intensity, charge state, mass-to-charge ratio (m/z), or isotopic pattern, and/or the presence of ion species in peak inclusion/exclusion lists. For example, a top-N criteria may be used, wherein the top N ion species based on intensity are selected (N can be any suitable number, e.g. 5, 10, 20, 50, 100, or higher), along with peak inclusion and/or exclusion lists. The mass selection window for the DDA mass analysis can be 1 m/z unit or narrower, or 0.8 m/z units or narrower.

The MS2 mass spectra contain fragment ion peaks corresponding to fragment ions derived from the structure of the peptides (structure-specific fragment ions) and reporter ion peaks corresponding to reporter ions derived from the (TMT) mass tags attached to the peptides. Typically, precursor ion peaks of unfragmented peptides are also present in the spectra. The MS2 mass spectra acquired by the DDA mass analysis are preferably utilised to form a spectral library of the peptides comprising precursor-specific fragment ion peaks extracted from the MS2 spectra as described in more detail below.

The LC-MS analysis comprises acquiring MS2 mass spectra of the multiplexed sample using data-independent acquisition (DIA) as shown in step 106 of FIG. 2. In embodiments in which DDA analysis is preferably performed first, DIA is thus performed in addition. The DIA and DDA are performed in separate runs. Preferably, the DIA is performed after the DDA. The LC-MS analysis thus comprises eluting the (tagged) multiplexed sample (typically a portion thereof) from the liquid chromatographic device, such as a chromatographic column, and acquiring MS2 mass spectra by performing data independent acquisition (DIA) of the tagged multiplexed sample as it elutes from the liquid chromatographic device. The DIA MS2 mass spectra contain fragment ion peaks corresponding to fragment ions (structure-specific fragment ions) derived from the structure of the peptides isolated in the mass isolation (selection) window and reporter ion peaks corresponding to reporter ions derived from the (TMT) mass tags attached to the peptides. Typically, precursor ion peaks of unfragmented peptides are also present in the spectra.

The DIA comprises multiple cycles of analysis as the sample elutes. Each DIA cycle comprises a set of (data-independent) MS2 scans. The (precursor) mass isolation windows of the DIA MS2 scans have a width that is greater than the width of the (precursor) mass isolation windows of the DDA MS2 scans, typically at least 2×, or 5×, or 10×, or 20× as great. The mass isolation windows of the DIA MS2 scans, for example, can have a width in the range from 2 m/z units to 25 m/z units, or from 5 to 20 m/s units or from 10 to 20 m/z units, e.g. a width of 2, 4, 6, 8, 10, 15, 20 or 25 m/z units. Commonly, a 10 m/z unit width window or a 20 m/z unit width window is used. The mass isolation windows can have fixed or variable widths, typically fixed. The mass isolation windows of the DIA MS2 scans can be overlapping or non-overlapping with respect to neighbouring windows. The set of DIA MS2 scans covers substantially the mass range of interest of the peptides in the multiplexed sample (for example, the width of an MS1 scan, which may be approximately 200 to 2000 m/z units, or 300 to 1500 m/z units, or 400 to 1200 m/z units, for example). The retention times (RT) are recorded for each of the DIA MS2 scans. The peptides represented in the DIA MS2 spectra can be found in a conventional step using a spectral library or database. Peptide spectral libraries and databases that have been acquired with TMT labeled peptides are not known to be publicly available. Existing libraries have been generally acquired with label-free methods (e.g. Peptide Mass Spectral Libraries, MassIVE-KB Peptide Spectral Libraries). A preferred library approach for the present method comprises using the data from the DDA analysis as now described.

The MS2 mass spectra acquired by the DDA mass analysis are preferably utilised to form a spectral library comprising mass spectral data (MS2 mass spectra) for a plurality of peptides and their fragment ions from the MS2 spectra acquired by DDA, as shown in step 108. The spectral library thus comprises peptide precursor-specific fragment ions extracted from the MS2 spectra. The spectral library typically contains for each of a plurality of peptide precursors: the m/z value (from the MS1 'survey' spectrum and/or MS2 isolation window) of the peptide and the m/z of its specific fragment(s) from the MS2 scans. The spectral library further typically contains the RT for each of the plurality of peptides (and associated fragment ions).

Peptides may be identified in the DDA MS2 spectra by a database search and/or de novo sequencing. For example, MaxQuant with the *Andromeda* search engine can be used in the creation of the spectral library, although any suitable search engine can be used. Identified fragment ions that are associated with a specific identified peptide precursor, e.g. from the database search, are included in the library (identified peptides). Some isolated and fragmented precursor ions in the DDA analysis may not be identified using the database search, e.g. those originating from the so-called dark proteome. Fragment ions associated with an unidentified precursor are preferably also included in the spectral library (as unidentified peptides). If the non-identified peptides are not included it can lead to biased deconvoluted TMT intensities in the later steps. In some embodiments, the use of a combination of a broad database search and de novo sequencing can allow identification and creating a spectral library for most (for example >80%) of the peptides that triggered MS2 scans in the DDA analysis.

The DDA spectra used for the spectral library are preferably subject to one or more processing steps or curation to clean up the spectra. In some embodiments, unspecific fragments ions (not associated to a peptide precursor) in the DDA MS2 spectra can be removed from inclusion in the spectral library. This may include one or more, preferably all, of: (TMT) mass tag reporter ions, complementary (TMT) mass tag ions, y1 precursor fragments, and remaining precursor ions. Prior to inclusion of fragment ions in the library, the DDA MS2 spectra are preferably deisotoped, for example by applying the algorithm published in Yuan, Z., Shi, J., Lin, W., Chen, B. & Wu, F. X. Features-based deisotoping method for tandem mass spectra. *Adv. Bioinformatics* 2011, (2011). Other deisotoping methods can be used, such as Decon2LS (N. Jaitly, A. Mayampurath, K. Littlefield, J. N. Adkins, G. A. Anderson, and R. D. Smith, "Decon2LS: an open-source software package for automated processing and visualization of high resolution mass spectrometry data," *BMC Bioinformatics*, vol. 10, article 87, 2009) and ICR2LS (C. Masselon, L. Pasa-Tolic, S. W. Lee et al., "Identification of tryptic peptides from large databases using multiplexed tandem mass spectrometry: simulations and experimental results," *Proteomics*, vol. 3, no. 7, pp. 1279-1286, 2003.), which use the THRASH algorithm (D. M. Horn, R. A. Zubarev, and F. W. McLafferty, "Automated reduction and interpretation of high resolution electrospray mass spectra of large molecules," *Journal of the American Society for Mass Spectrometry*, vol. 11, no. 4, pp. 320-332, 2000).

In some embodiments, fragment ions, i.e. those remaining in the spectra after removal of unspecific fragment ions, and deisotoping, are binned into a plurality of m/z ranges, preferably with equal m/z width, spread across the precursor mass range of interest. The peaks of fragment ions with the highest intensities in each bin are determined and a plurality of the most intense ions are kept for the library as they are most likely to be precursor-specific. The other fragment ions peaks are removed. Curation of the spectral library may also comprise removing duplicated MS2 spectra. Thus, in some embodiments, duplicated spectral library entries are removed. For example, all spectra within a given retention time window (e.g. 2 minutes) and having a precursor ion m/z difference within a predetermined tolerance (e.g. $10^4$ ppm) are compared and given a spectrum matching score. If the matching score is above a predetermined threshold (i.e. the match is closer than a threshold), the more intense spectra is kept for the library. Many methods for determining a matching score are known in the art. A preferred matching score for this aspect is the Hyperscore described in Searle, B. C. et al. Chromatogram libraries improve peptide detection and quantification by data independent acquisition mass spectrometry. *Nat. Commun.* 9, 1-12 (2018).

Thus, in particular embodiments, forming the spectral library can include processing the MS2 spectra acquired by DDA, wherein the processing comprises one or more of the following:
(i) removing peaks representing ions that are not specific to a biomolecule;
(ii) deisotoping the spectra;
(iii) binning peaks of fragment ions of the biomolecules into a plurality of m/z bins and keeping a predetermined number of the most intense peaks;
(iv) removing duplicate spectra.

In the LC-MS data, there are typically many peptides that are not identified in DDA MS2 mass spectra but that nonetheless are relatively abundant, e.g. originating from the dark proteome. The number of such peptides can be as much as 25-30% of the total in some cases. These peptides contribute to the overall mass tag (TMT) reporter ion intensity but since their specific MS2 fragment ions are unknown it is a problem to deconvolute their contribution.

To address this problem, a preferred approach is now described. The mass spectra in the spectral library for identified peptides are obtained by first finding peaks in MS1 spectra acquired by the data-dependent acquisition (DDA), then finding peaks of fragment ions in the MS2 spectra acquired by DDA that correlate with the peaks in the MS1 spectra based on retention time (within a tolerance), and subsequently identifying structures of the peptides based on the peaks in MS1 and the correlating peaks of fragment ions. As described above, identifying peptides based on their correlated precursor and fragment ion peaks typically comprises searching a database or library. MaxQuant is one example of such database but others are available. The MS2 spectra can be first deisotoped, which simplifies the spectra. Generally, the precursor peptide ions (e.g. from MS1 spectra) are found from the spectra and fragment ions that correlate with each precursor are identified. In some embodiments, MS1 (survey) spectra (from the DDA mass analysis of the samples) can be used to identify isotopic clusters or distributions of peaks that may belong to peptides (for example that are suitable or expected isotopic clusters for peptides based on their m/z and z). Thus, finding peaks in the MS1 spectra typically comprises identifying isotopic clusters in the MS1 spectra that are expected to belong to peptides. For each identified isotopic cluster, the fragment ions (in DDA spectra) are found that correlate with it based on retention time. In some cases, one and the same fragment ion can correlate with more than one identified isotopic cluster, e.g. because of different charge states of the precursor ion. This is not a problem since at this stage the correlation list of fragments can be broad and contain false positive fragments, which can be cleaned up subsequently. Peptides (i.e. structures/sequences) can then be identified using a combination of the MS1 data for the peptide precursor found and the correlated fragment ions, or using other methods. Preferably, the mass spectra in the spectral library for the identified peptides comprise only correlating peaks of fragment ions that are supported by the identified structures. Correlating peaks of fragment ions that are not supported by the identified structures are preferably removed from the mass spectra of the identified peptides forming the spectral library. As mentioned, as well as the identified peptides, there are typically a number of unidentified peptides (e.g. from the dark proteome). These can preferably also be used for the deconvolution. Correlating fragment ions that are not supported by the identified structures of the peptides can be used to represent unidentified peptides in the spectral library. In one approach, for the identified peptides, the list of correlating fragment ions can be checked and only those that are supported by the identified peptide structures/sequences are kept (as associated with those identified peptides). For the unidentified peptides, the (each) list of correlating fragment ions is checked and only those that are unique and are not associated with simultaneously eluting identified peptides are kept as representing unidentified peptides. For example, from a given list of correlating fragment ions, those that are unique and not associated with any simultaneously eluting identified peptides are used for representing an unidentified peptide. Then both identified and unidentified peptides, i.e. their fragment ions, can be used for the deconvolution of the abundances of the mass tag (TMT) reporter ions.

Another practical approach to the problem of peptide identification comprises using a combination of a (very broad) database search together with de novo sequencing using a software such as PEAKS (Bioinformatics Solutions Inc), accepting any hits. This has been found in some embodiments to allow creating a spectral library for >80% of all the peptides that triggered MS2 scans in the DDA, and use these to deconvolve peptide abundances in the reporter ion abundance. Another approach is an open modification search using a search tool such as MSFragger (e.g. A. T. Kong et al, *Nature Methods*, vol. 14 (2017), pages 513-520).

The present disclosure has particular application to single cell proteomics (SCP), i.e. in which individual samples in the multiplexed sample are each derived from a single cell, i.e. single cell proteomes. In particular embodiments, therefore, the samples of the multiplexed mixture are each comprising peptides produced by digestion of a single cell proteome. It can be assumed that the identities of the peptides are the same in all the single cell proteomes but their abundances are different. In SCP, the main aim is subgroup differentiation of cells, based on the abundances in the cells of the same group of proteins or peptides. Separation or differentiation of subgroups of cells (i.e. grouping cells into different subgroups) can be performed by determining their signature profiles (i.e. their abundance profiles of the same group of proteins or peptides) and grouping cells with similar profiles. Therefore, inaccuracy in measuring relative peptide abundances in SCP only results in less clear differentiation of the cell subgroups, which may still be sufficient for subgroup differentiation. In some embodiments, therefore, the task of peptide identification in the DIA-obtained MS2 data from single cell proteomes can be limited to the DDA-obtained library of precursor m/z, RT and fragment ions.

After cell subgroup identification, it will become clear which peptides contribute most in such differentiation (herein termed "subgroup-specific peptides"), after which single cell proteome analysis can be performed again (on another cell population, which may still containing the same subgroups) by a targeted method aiming at analysing these subgroup-specific peptides, which characterise the subgroups. Moreover, it is known that for subgroup differentiation, it is often enough to analyse the abundances of several hundred most abundant proteins. Therefore, the ability to identify and quantify with modest accuracy say, ≤1000 proteins, or ≤10,000 peptides, would be sufficient to fulfill the requirements for SCP in most situations.

Accordingly, in an aspect of the present disclosure, there is provided a method of differentiation of cells, which comprises the method of mass spectrometry according to the disclosure. Single cell samples, i.e. samples containing single cell proteomes, can be digested to generate samples containing peptides. The samples can be respectively mass tagged (TMT) and mixed to form a multiplexed sample for analysis by the method of mass spectrometry. The deconvoluted reporter ion abundances determined The DIA MS2 mass spectra contain fragment ion peaks corresponding to fragment ions derived from the structure or sequence of the eluting peptides (structure-specific fragment ions, also termed sequence-specific fragment ions) and simultaneously reporter ion peaks corresponding to reporter ions derived from the mass tags attached to the eluting peptides. A problem with using the relative abundances of the reporter ions for quantifying the relative peptide abundances, and thus relative protein abundances, in the respective samples that have been multiplexed is that the relatively wide mass isolation windows used for DIA (e.g. 10-20 m/z units) means that the reporter ion intensity or abundance is often the result of multiple co-fragmented peptides (so called chimeric mass tag spectra). Deconvolution of the (TMT) reporter ion intensity from multiple co-fragmented peptides is therefore required.

Peptides can be found or identified from the DIA MS2 spectra using a spectral library, i.e. matched with peptides in the spectral library, preferably the spectral library obtained from the DDA mass analysis of the multiplexed sample in the way described above, as shown in step 110 of FIG. 2. This approach addresses the lack of a publicly available TMT labeled spectral library. In an alternative, it may be possible to transform an existing TMT labeled sample into a spectral library. It may also be possible in the future to use an in-silico generated DIA library. However, such approaches will not include unidentified fragment ions from the dark proteome, which has been found to be advantageous for the successful deconvolution of the mixed TMT signals.

Peaks due to (structure-specific) fragment ions of the peptides in the DIA MS2 spectra are matched to peaks of fragment ions in the MS2 spectra in the (DDA) spectral library. Accordingly, DIA spectra can be matched to library spectra and thus the peptides in the DIA spectra found. Thus, the step of finding or identifying peptides from fragment ion peaks of the DIA MS2 spectra comprises matching fragment ions of the DIA MS2 spectra to fragment ions of the spectral library (i.e. matching fragment ion peaks in the DIA MS2 spectra to peaks in the library spectra). Preferably, each library (MS2) spectrum is matched against the DIA spectra. The matching between the DIA MS2 fragment ions and the library fragment ions, can be determined by numerous methods as known in the art in order to find the closest match. The matching is typically based on the difference in m/z (mass error) of the (peaks of) fragment ions in the DIA versus the library spectra. Optionally other factors can be used in the determination of matches, for example, the difference in retention time, precursor m/z and the like. In this way, peptides are matched between the DIA MS2 spectra and the MS2 spectra in the spectral library.

Prior to matching fragment ions of the DIA MS2 spectra to the fragment ions in the (DDA) spectral library their retention times are preferably aligned. Retention time alignment methods are well known in the art. For example, precursor (MS1) peaks can be extracted, such as with the Dinosaur tool (Teleman, J., Chawade, A., Sandin, M., Levander, F. & Malmström, J., Dinosaur: A Refined Open-Source Peptide MS Feature Detector. *J. Proteome Res.* 15, 2143-2151 (2016), compared and the retention time aligned by applying a linear correlation model.

In preferred embodiments, library (MS2) mass spectra are each matched against the DIA mass spectra in a retention time window, preferably a defined retention time window around (preferably centered on) the retention time of the library spectra. Preferably, this is based on the corrected (aligned) retention time. For a typical LC-MS experiment, each library (DDA) spectrum can be matched against each of the DIA spectra in a retention time window of several minutes, preferably 1 to 5 minutes, or 2 to 4 minutes, such as a 3 minute retention time window (i.e. spanning 1.5 minutes either side of the retention time of the library spectrum). Fragment ions (i.e. their peaks) are preferably matched if they lie within a predetermined mass tolerance of each other, e.g. a 10 ppm tolerance. The tolerance limit can be, for example, 15 ppm or less, 10 ppm or less, or 5 ppm or less. If multiple fragment ions in the DIA spectra are identified as matching within the tolerance, the fragment ion with the lowest mass error is typically considered further as a match. In some embodiments, matching of fragment ion peaks may also be based on further criteria in addition to the mass error, for example an intensity error and/or retention time error. In some embodiments, in order to assess the probability of a true match, for each library spectra, a series (i.e. two or more) of probability scores can be calculated at each time point in the retention time window (each DIA MS2 spectra being acquired at a respective time point). Thus, each (DDA) library spectrum is scored against each DIA MS2 spectrum in the defined retention time window. The scores can be used to determine the elution profile of the peptide. This series of probability scores can include, in one example, a spectra matching score such as a 'Hyperscore' (Searle et al, above), the (intensity) sum of all (matched) fragment ions (sum-intensity), and/or the number of matched fragment ions. The series of probability scores can be used as criteria to remove a number of spectra matches from further processing, i.e. remove the spectra from further consideration in the matching (e.g. remove from determining the 'fragment ion sum' described below and thus remove from quantitatively deconvoluting reporter ions abundances). As an example of removing spectra matches from further processing based on the series of probability scores, all spectra matches with a maximal matching score (Hyperscore) less than a threshold value and preferably with less than a threshold number of matched fragments are removed from consideration. For example, in one embodiment, all spectra matches with a maximal Hyperscore <2 and less than 3 matched fragment ions can be removed.

For quantitatively deconvoluting the abundancies of the mass tag reporter ions, for each matched library spectrum (i.e. each matched peptide), a sum of intensities of matched (i.e. structure-specific) fragment ions in the DIA spectra is determined (termed herein 'fragment ion sum'). This sum, preferably including the molecular ion intensity, represents the (total) peptide abundance for that peptide. Thus, the method comprises determining an abundance for each found peptide represented by an MS2 mass spectrum in the spectral library matched to one or more MS2 spectra acquired by DIA as shown in step 112. This abundance is determined by summing intensities of matched peaks of fragment ions in the MS2 spectra acquired by DIA. Preferably, calculating the sum of intensities comprises calculating the sum of the intensities of matched peaks of fragment ions in the DIA MS2 spectra in a defined retention time interval. The fragment ion sum represents the peptide precursor abundance used for the quantitative deconvolution of relative abundances of the peptides from the reporter ions.

Preferably, for quantitatively deconvoluting the abundancies of the mass tag reporter ions, an optimum is determined for the defined retention time interval in which the abundance for each peptide is determined ('optimum retention time interval'), i.e. for determining the fragment ion sum. The method thus preferably comprises a step of determination of an optimal retention time (RT) interval (for each peptide) for deconvolution of the reporter ion (mass tag) abundances. This optimal time interval may be determined in different ways.

In one method, the apex of the elution for each (matched) peptide is determined and a plurality of DIA MS2 spectra either side of the apex are utilised for the quantitation subsequently, i.e. deconvolution of the reporter ions. In this way, the apex of the elution is determined and an optimal time interval is based on (e.g. centered on) the apex. The apex can be found in different ways. In some embodiments, finding the apex is based on calculating a further score for each DIA MS2 spectra. Such score can be based on a matching score (e.g. Hyperscore) and sum-intensity for the fragment ions. Such score can be based on a combination of any of the probability scores. A rolling median of the score over a plurality of (usually several) time windows can be calculated. For example, in one embodiment, first a rolling median over a plurality of (usually several) time windows can be calculated based on a formula such as: Hyperscore$^2$*log 10(sum-intensity). The DIA spectra with the highest score can be considered to be at the apex of the elution. One or more (preferably a plurality of) DIA spectra either side of the apex, thereby defining an optimum retention time interval, are then considered for the next steps. For example, ±1 DIA spectra, ±2 DIA spectra, ±5 DIA spectra, ±10 DIA spectra, ±20 DIA spectra etc. can be considered. A fragment ion sum is calculated for (matched) fragment ions in the thus defined time interval for each peptide. The fragment ion sum is calculated as the sum of the intensities (i.e. abundances) of the fragment ions. The fragment ion sum represents the total peptide precursor abundance.

This sequence of steps can be refined further. For example, a peak shape model, such as a Gaussian model, optionally can be fitted for the intensity of each (matching) fragment ion through the time points (of MS2 spectra) in the time interval, and fragment ions with a correlation, e.g. an $R^2$ (coefficient of determination), below a threshold (e.g. $R^2<0.85$) for the model can be removed, i.e. removed from further consideration or processing. The removed fragment ions may not be included, for example, when calculating the fragment ion sum as above. In addition, or alternatively, there can be a step of calculating a median intensity of all matched peaks of fragment ions in the DIA MS2 spectra, and correlating each fragment ion intensity against the median, wherein fragment ions not having a correlation above a threshold (e.g. $R^2>0.90$) are removed again. Thus, the fragment ions removed here may not be included, for example, when calculating the fragment ion sum as above. In addition, or alternatively, a median intensity of all (remaining) fragment ions following the above steps optionally can be calculated, and each fragment ion intensity correlated against this median. In other words, fragment ions with a correlation above the threshold (e.g. >0.90) can be considered to be quantitative (i.e. assumed reliable for quantitation). Fragment ion abundances (of the quantitative fragment ions) are then summed up in order in the fragment ion sum to determine total precursor intensity (peptide abundance). The elution boundaries are determined based on the DIA window before the rolling median over the plurality of windows of Hyperscore*log 10(sum-intensity) drops below 5% compared to the apex one.

An alternative approach for determination of the optimal RT interval can be used in the embodiments in which the $X^{th}$ sample in the multiplexed sample is a pool of the $1^{st}$ to $(X-1)^{th}$ individual samples. The determination of the optimal RT comprises selecting a retention time (RT) interval within the peptide's chromatographic elution peak that contains the best correlation between the sum of the intensities (abundances) of all the peptide's (matched) structure-specific fragment ions and the abundance of the reporter ions in the mass tag channel of the pooled sample. Thus, first, for each identified peptide, the sum of all sequence-specific fragments is determined for each of the DIA MS2 spectra within a RT window of the peptide's chromatographic peak elution. Then, a correlation, preferably a linear correlation such as a Pearson correlation, is calculated between that sum and the abundance of reporter ions in the $X^{th}$ mass tag channel (i.e. pooled sample) for each of multiple time intervals within the RT window, and the interval (containing at least 3 consecutive MS2 spectra) is chosen that gives the highest correlation. A fragment ion sum is then calculated (as described above) using the chosen interval.

From each DIA MS2 mass spectrum, abundances (intensities) of the mass tag reporter ions can be determined, as shown in step 114 of FIG. 2. An abundance of each of the reporter ions is thereby determined for the DIA MS2 spectra, preferably an abundance of each reporter ion for each DIA MS2 spectra. Preferably, the same DIA MS2 spectra are used for reporter ion abundances that are used in summing the intensities of the matched peaks of fragment ions to calculate the peptide abundances. Preferably, the abundance of each reporter ion is extracted from the spectra as the most intense peak in a narrow window (e.g. ±0.003 m/z units (Th) window) around the expected monoisotopic reporter ion mass.

The abundances of the reporter ions can be deconvoluted based on the determined abundances of the peptides (from the fragment ion sum for each peptide) as shown in step 116. This enables the relative abundances of each peptide in each peptide-containing sample to be determined. This quantification of peptide abundances in the individual peptide-containing samples is the desired outcome of the analysis. The disclosure may further comprise a step of identifying proteins from the peptide identifications and/or determining protein abundances from the peptide abundances. Thus, the individual contributions from co-fragmented peptides to the reporter ion abundance in the MS2 spectra can be deconvoluted. The present disclosure thus enables deconvolution of total (chimeric) reporter ion abundance in each MS2 spectra into reporter ion abundances resulting from each of multiple co-fragmented peptides. In particular, the peptide abundances deconvoluted from the reporter ions in the DIA data is accurate enough for single cell proteomics (SCP) purposes. For example, peptide abundances deconvoluted from the reporter ions are accurate enough to be used for cell subgroup differentiation. These deconvoluted abundances can be stored, e.g. on a computer storage medium, and/or output, e.g. in a user readable form, such as on a video display unit.

In preferred embodiments, abundances of the reporter ions are deconvoluted mathematically. For example, a set of linear equations are used for deconvoluting the abundances of the reporter ions. The set of linear equations can be constructed and solved to find the relative abundances of each (matched) peptide in the peptide-containing samples of the multiplexed sample. The linear equations can be solved using matrices. The linear algebra is based on the principle that the abundance of a given reporter ion (representing the abundance of all peptides in a given one of the peptide-containing samples) can be expressed as a linear combination of the abundances of each peptide in the given peptide-containing sample, at a given retention time. In turn, the abundance of each peptide in the given sample at the given retention time can be expressed as the (total) abundance of the peptide for all samples, i.e. for all mass tags (which has been determined by the method described herein), multiplied by the relative or fractional abundance of the peptide in the given sample (i.e. the abundance of the peptide in the given sample relative to the abundances in the other samples). The relative or fractional abundance of the peptide in the given sample can thereby be deconvoluted from the reporter ion abundance by solving the equations. Thus, in preferred embodiments, each linear equation relates an abundance of a reporter ion of one of the peptide-containing samples to a linear combination of abundances of each peptide in that peptide-containing sample (at a given retention time), wherein the abundance of each peptide in that sample is expressed as the (total) abundance of the peptide for all mass tags, i.e. in all the peptide-containing samples, multiplied by the relative abundance of the peptide in that peptide-containing sample. The abundance of each reporter ion can be determined from the DIA MS2 spectra, i.e. for each retention time. The (total) abundance of each peptide for all mass tags, i.e. in all the peptide-containing samples, likewise can be determined from the spectra (as the described fragment ion sum), also for each retention time. Therefore, the equations can be solved to find the relative abundance of each peptide in each peptide-containing sample (reporter ion). In practice, for multiplexed samples comprising multiple different tags giving rise to respective reporter ions, each equation can relate abundances of a plurality of respective reporter ions at the respective retention time to a linear combination of the (total) abundances of the (matched) peptides, i.e. abundances of the (matched) peptides across all the peptide-containing samples.

A simple example of the construction of such a linear equation system is shown in equations 1a, 1b and 1c, for a single tandem mass tag channel 126 (m/z 126) in a multiplexed sample in which two peptides A and B co-elute and are co-isolated and fragmented in the DIA MS2 scans):

$$TMT126(t1) = pepA(t1)*TMT126(A) + pepB(t1)*TMT126(B) \quad (1a)$$

$$TMT126(t2) = pepA(t2)*TMT126(A) + pepB(t2)*TMT126(B) \quad (1b)$$

$$TMT126(t3) = pepA(t3)*TMT126(A) + pepB(t3)*TMT126(B) \quad (1c)$$

where:
TMT126 (t1) is the abundance of the 126 mass tag reporter ion at retention time t1; pepA(t1) is the (total) abundance of peptide A at time retention t1; pepB(t1) is the (total) abundance of peptide B at time retention t1; TMT126(A) is the relative or fractional abundance of peptide A in the sample tagged with the 126 mass tag; TMT126(B) is the relative or fractional abundance of peptide B in the sample tagged with the 126 mass tag; and t2 and t3 respectively refer to retention times t2 and t3.

In particular embodiments, a plurality of reporter ions are measured from respectively mass tagged samples that are multiplexed and abundances of these reporter ion are deconvoluted. A separate linear equation can be constructed for each respective retention time. Each of the equations relates (equates) the abundances of the reporter ions at a respective retention time to a linear combination of the (total) abundances of the (matched) peptides for all mass tags (i.e. across all the peptide-containing samples) at the respective retention time. The (total) abundance of each peptide for all mass tags can be expressed as a linear combination of the abundances of the peptide in each of the peptide-containing samples. Thus, each of the equations relates (equates) the determined abundances of the reporter ions to a linear combination of the abundances of the peptides in each of the peptide-containing samples at the respective retention time. For each of the samples, the abundance of each peptide in each sample can be expressed as the determined (total) abundance of the peptide across all samples multiplied by the relative or fractional abundance of the peptide in that sample.

Thus, deconvolution of the abundances of the reporter ions can comprise using the determined abundances of the respective reporter ions and the determined total abundances of the biomolecules at corresponding retention times of the plurality of retention times to determine the relative or fractional abundances of each matched biomolecule in each biomolecule-containing sample.

Generally, a set of M linear equations can be constructed for N peptides (N typically <10,000; M=number of DIA MS2 scans; M≥N*X, with X being the number of MS2 scans (for a specific DIA window), with each peptide having X individual components (so, there are X independent parameters for N peptides, thus X*N independent parameters in total). Each equation links the abundance of one of the reporter ions with the total abundance of each peptide (as determined from the sum of fragment-specific ions for each peptide).

According to some preferred embodiments, the deconvolution with linear algebra can be solved by constructing two matrices. A first matrix comprises all of the reporter ion abundances (intensities) as columns (i.e. each reporter ion has its abundances in a separate column of the matrix) and all of the DIA spectra retention times as rows (i.e. each retention time is a separate row). The second matrix, comprises all of the (total) peptide abundances as columns (i.e. each peptide has its abundances in a separate column of the matrix) and, again, all of the DIA spectra retention times as rows (i.e. each retention time is a separate row). For example, in the simplified case above, for the single TMT channel 126 and two peptides A and B, the linear equations 1a, 1b and 1c can be written in matrix form as:

$$\begin{bmatrix} TMT126(t1) \\ TMT126(t2) \\ TMT126(t3) \end{bmatrix} = \begin{bmatrix} pepA(t1) & pepB(t1) \\ pepA(t2) & pepB(t2) \\ pepA(t3) & pepB(t3) \end{bmatrix} \begin{bmatrix} TMT126(A) \\ TMT126(B) \end{bmatrix}$$

The first matrix $$\begin{bmatrix} TMT126(t1) \\ TMT126(t2) \\ TMT126(t3) \end{bmatrix}$$

comprises the reporter ion abundances as a column (a single column as there is a single TMT channel) and the DIA spectra retention times as rows.
The second matrix $$\begin{bmatrix} pepA(t1) & pepB(t1) \\ pepA(t2) & pepB(t2) \\ pepA(t3) & pepB(t3) \end{bmatrix}$$

comprises the peptide abundances as separate columns and the DIA spectra retention times as rows.
Solving the matrix algebra finds the values of the third (final) matrix $$\begin{bmatrix} TMT126(A) \\ TMT126(B) \end{bmatrix}$$

which gives the deconvoluted relative abundances of peptides A and B in the TMT channel 126.

Another simplified example of such matrices is shown with schematic data in Table 1 for a single TMT channel again and with three peptides A, B and C.

TABLE 1

| Retention time | Matrix 1 intensity_TMT126 | Matrix 2 | | |
|---|---|---|---|---|
| | | Peptide A | Peptide B | Peptide C |
| 1 | 9401.27066 | 0 | 45.71942 | 0 |
| 2 | 196290.3335 | 0 | 954.5817 | 0 |
| 3 | 1989910.331 | 0 | 9677.155 | 0 |

TABLE 1-continued

| Retention time | Matrix 1 intensity_TMT126 | Matrix 2 | | |
|---|---|---|---|---|
| | | Peptide A | Peptide B | Peptide C |
| 4 | 9794681.926 | 0 | 47632.62 | 0 |
| 5 | 23408274.66 | 0 | 113837 | 0 |
| 6 | 27162560.63 | 0 | 132094.5 | 0 |
| 7 | 15303622.69 | 0 | 74423.21 | 0 |
| 8 | 4186393.309 | 0 | 20358.9 | 0 |
| 9 | 556042.5704 | 0 | 2704.097 | 0 |
| 10 | 35859.00987 | 0 | 174.3863 | 0 |
| 11 | 23821.345 | 0 | 0 | 132.2039 |
| 12 | 497368.9116 | 0 | 0 | 2760.303 |
| 13 | 5042120.605 | 0 | 0 | 27982.81 |
| 14 | 24818187.43 | 0 | 0 | 137736.2 |
| 15 | 59312895.75 | 0 | 0 | 329175.3 |
| 16 | 68925905.14 | 100.8531 | 0 | 381969.4 |
| 17 | 40869854.84 | 2105.724 | 0 | 215204.9 |
| 18 | 31824373.64 | 21346.96 | 0 | 58870.52 |
| 19 | 105841230.1 | 105073.4 | 0 | 7819.264 |
| 20 | 249673247.5 | 251114.6 | 0 | 504.2619 |
| 21 | 289611122.7 | 291389.1 | 0 | 0 |
| 22 | 163169423.1 | 164171.2 | 0 | 0 |
| 23 | 44635926.73 | 44909.96 | 0 | 0 |
| 24 | 5928605.746 | 5965.003 | 0 | 0 |
| 25 | 382333.9134 | 384.6812 | 0 | 0 |

A simplified example for the two TMT channels 126 and 127 and two peptides A and B requires four parameters to be found: TMT126(A), which is the relative or fractional abundance of peptide A in the sample tagged with the 126 mass tag; TMT126(B), the relative or fractional abundance of peptide B in the sample tagged with the 126 mass tag; TMT127(A), the relative or fractional abundance of peptide A in the sample tagged with the 127 mass tag; and TMT127(B), the relative or fractional abundance of peptide B in the sample tagged with the 127 mass tag. The four parameters require four (or more) equations to find their values, which can be expressed with matrices as:

$$\begin{bmatrix} TMT126(t1) & TMT127(t1) \\ TMT126(t2) & TMT127(t2) \\ TMT126(t3) & TMT127(t3) \\ TMT126(t4) & TMT127(t4) \end{bmatrix} =$$

$$\begin{bmatrix} pepA(t1) & pepB(t1) \\ pepA(t2) & pepB(t2) \\ pepA(t3) & pepB(t3) \\ pepA(t4) & pepB(t4) \end{bmatrix} \begin{bmatrix} TMT126(A) & TMT127(A) \\ TMT126(B) & TMT127(B) \end{bmatrix}$$

It can be seen from the above that, in preferred embodiments, deconvoluting relative abundances of the peptides in each peptide-containing sample from the abundances of the reporter ions comprises solving matrices, for example to solve the linear equations. In preferred embodiments, the deconvolution comprises constructing matrices, wherein a first matrix (M1) comprises the determined abundances of the respective reporter ions as columns with the retention times corresponding to the rows and a second matrix (M2) comprises the determined total abundances of the (respective) matched peptides as columns with the retention times corresponding to the rows. A third matrix (M3) can comprise the relative abundances of the peptides in each peptide-containing sample. The third matrix can comprise the relative abundances of the peptides in each peptide-containing sample as columns with the (respective) peptides corresponding to the rows. The relative abundances of the peptides in each peptide-containing sample can be found from solving the formula M1=M2*M3.

For deconvoluting the chimeric reporter ion abundances, least squares regression can be used. In one embodiment, the Stark-Parker implementation of bounded-variable least squares algorithm has been used (Stark, P. B. & Parker, R. L. Bounded-Variable Least-Squares: an Algorithm and Applications. https://www.stat.berkeley.edu/~stark/Preprints/bvls.pdf).

Figure 3:
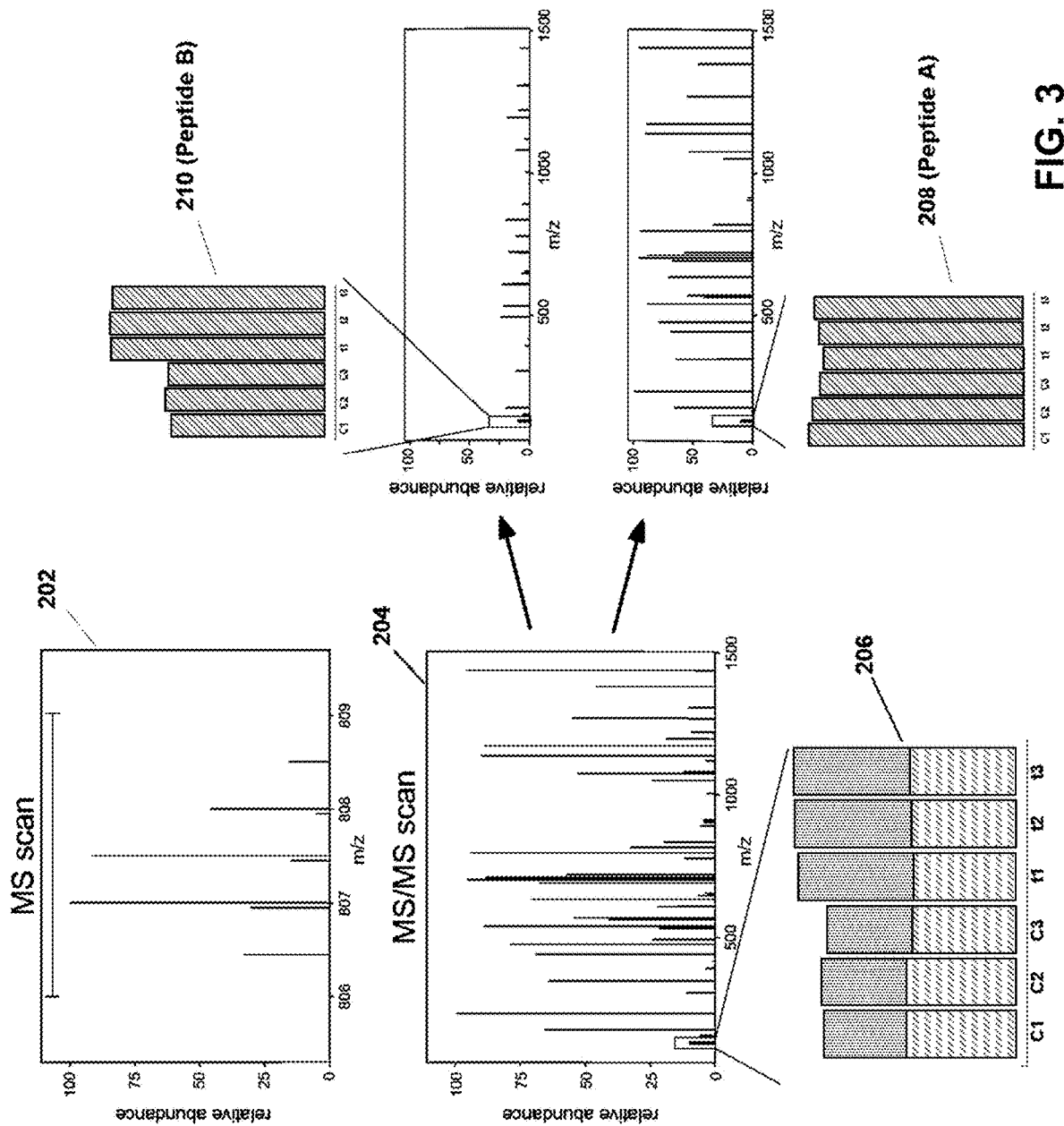
FIG. 3 shows schematically mass chromatogram, MS2 spectra of two co-isolated peptides A and B and their respective TMT intensities.

An illustration of the method is provided with reference to FIG. 3. A 6-plex TMT tagged multiplexed sample is analysed by LC-MS. Isotopic peaks dusters are identified with overlapping elution profiles in a mass chromatogram (RT versus m/z). In a particular DIA isolation window 202 during elution, two different peptides A and B are co-isolated and co-fragmented. From the chimeric DIA MS2 spectrum 204 of the co-fragmentation, the six reporter ions (labelled c1, c2, c3, t1, t2, t3) representing the peptide abundances in the individual samples are observed but each observed reporter ion abundance (intensity) 206 is an aggregate of the reporter ions from peptide A and peptide B. What is desired to be determined are the individual abundances of peptides A and B in each sample. These can be found using narrow isolation windows, as used in a DDA scan, to isolate each peptide individually. The reporter ion abundances 208 are shown for peptide A and reporter ion abundances 210 are shown for peptide B. It can be seen that the combination of reporter ion abundances 208 and 210 for the individual peptides gives the reporter ion abundances 206 for the co-fragmented DIA spectrum.

Figure 4A:
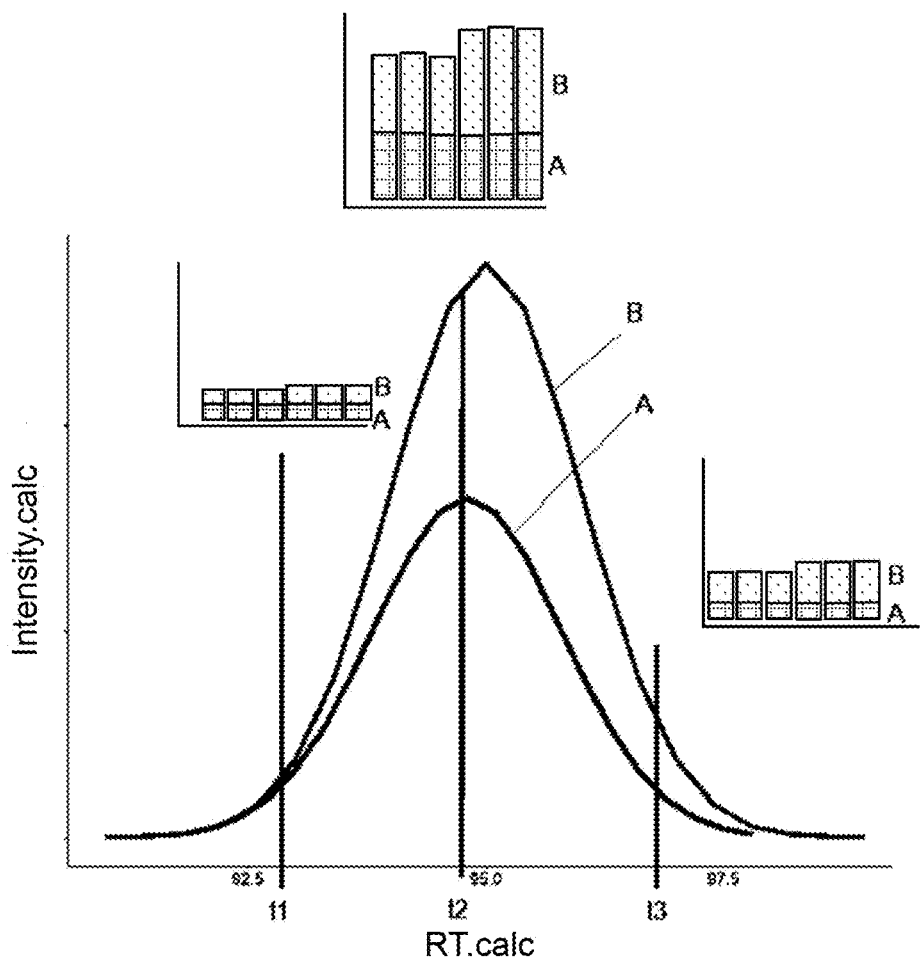
FIG. 4A shows elution profiles for the two peptides A and B.
Figure 4B:
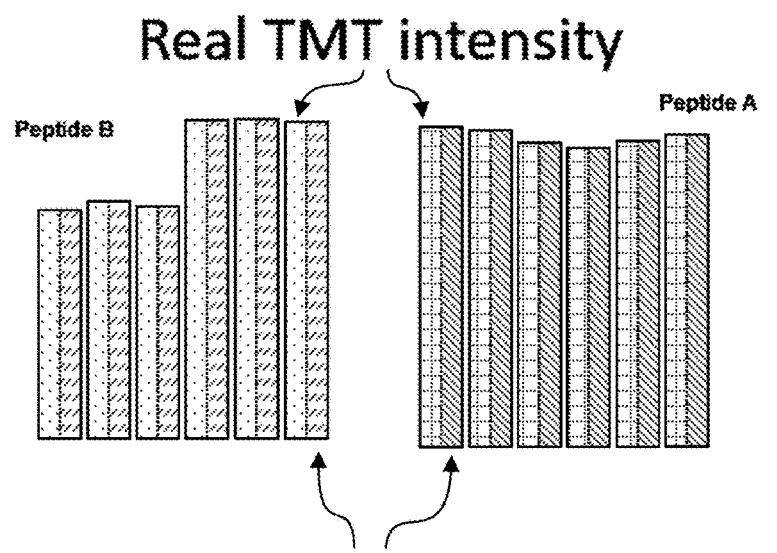
FIG. 4B shows deconvoluted TMT reporter ion abundances compared to real TMT abundances for the two peptides A and B.

In FIG. 4A is shown calculated elution profiles for the peptides A and B. At times t1, t2 and t3 as shown on the elution profiles, the relative contributions to the total reporter ion abundance from peptides A and B varies. At time t1 the abundances of peptides A and B are approximately the same but at times t2 and t3 peptide B has a higher abundance and so a relatively higher contribution to the total reporter ion abundance (shown by the plots of reporter ion abundances at each time). Such time-varying contribution of peptide abundances from each eluting peptide to the reporter ion abundance is utilised in constructing a system of linear equations of the general form described above, for example as shown above in equations 1a, 1b and 1c. Through determining from the DIA MS2 spectra the abundance of each reporter ion at each retention time, together with determining the (total) abundance of each peptide at each retention time, it becomes possible to solve the linear equations to deconvolute each reporter ion abundance and so determine the relative abundance of each peptide in each sample. FIG. 4B shows that the deconvoluted TMT reporter ion abundances (intensities) reflect the real TMT abundances. The set of reporter ion abundances for TMT channels c1, c2, c3, t1, t2, t3 on the right in FIG. 4B are for peptide A and the set of reporter ion abundances on the left are for peptide B. In each TMT channel, two abundances are shown. The left abundance in each TMT channel is the real TMT intensity reflecting the relative abundance of the peptide in the sample and the right abundance is the deconvoluted TMT intensity from solving the linear equations. The two abundances, real and deconvoluted, are the same.

Figure 5A:
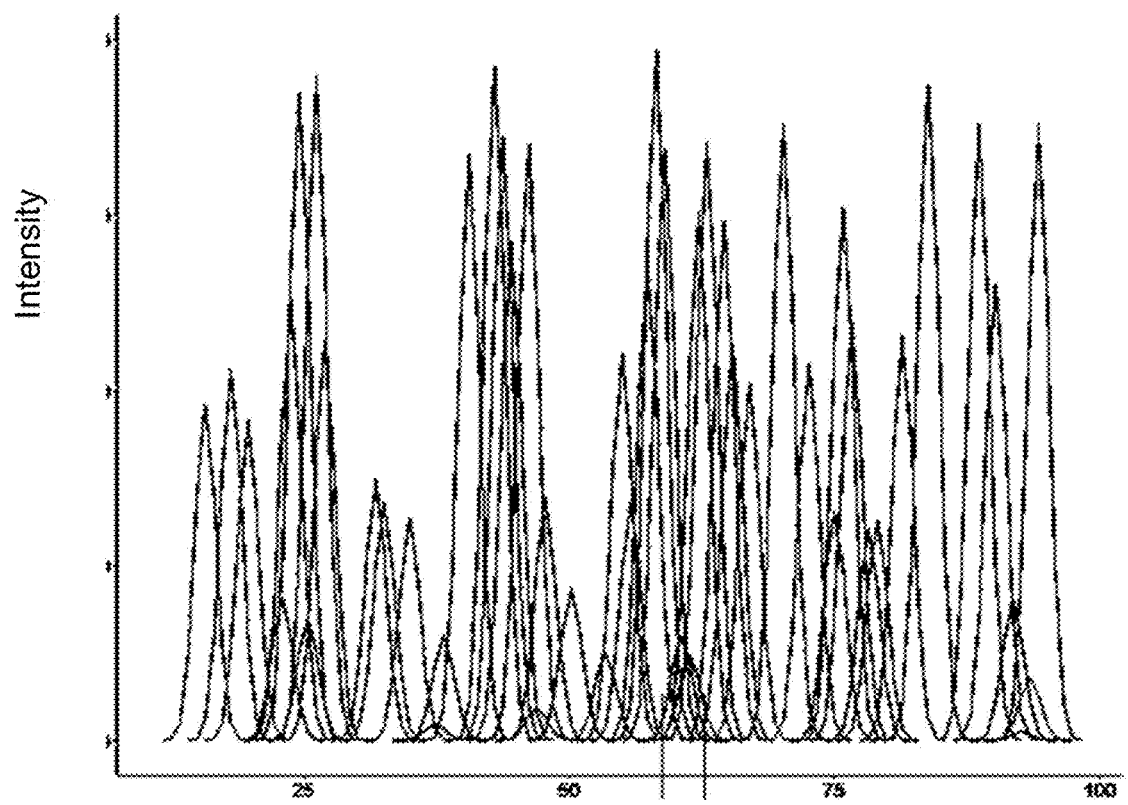
FIG. 5A shows a simulated chromatogram of 50 tagged peptides
Figure 5B:
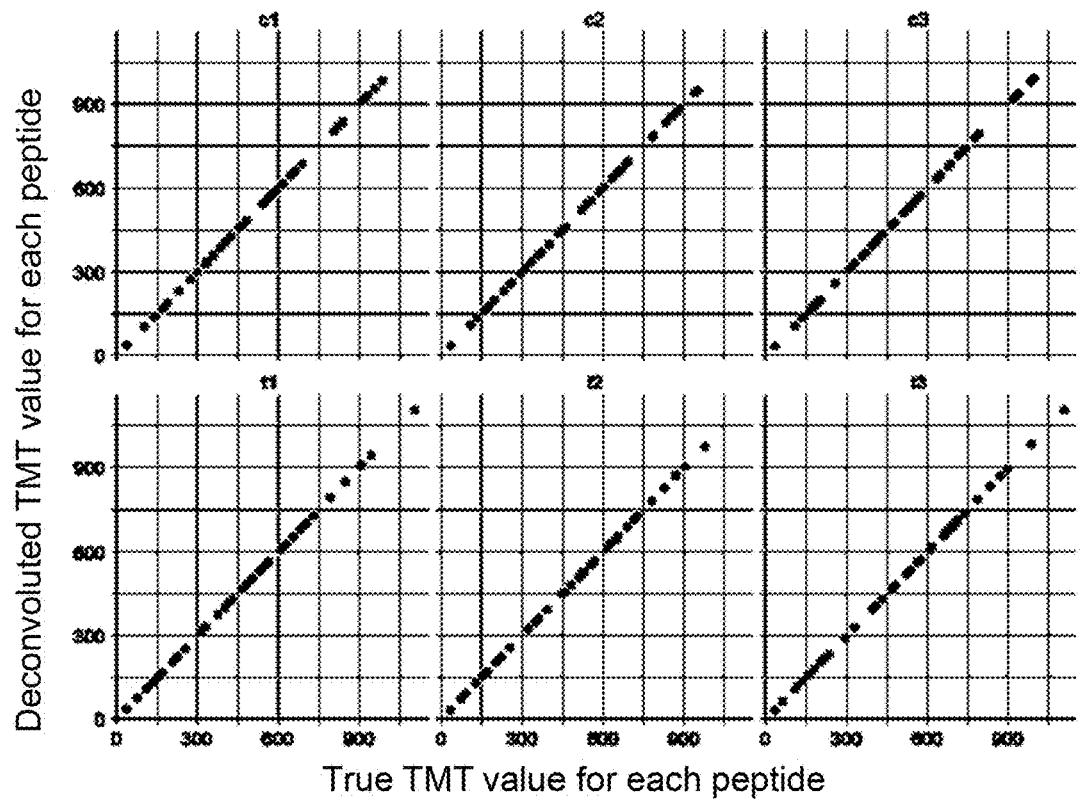
FIG. 5B shows plots of the deconvoluted TMT abundance value against the true TMT abundance value for each of the peptides from the chromatogram of FIG. 5A for each TMT channel.

A more complex in silico example of deconvolution using linear equations is shown with reference to FIGS. 5A and 5B. FIG. 5A shows a simulated chromatogram of 50 tagged peptides (intensity versus retention time, arb. units). DIA MS2 analysis was simulated with 3 second (s) cycles, i.e. each window scanned every 3s. For a 5 minute RT window of 101 data points, each peptide was sampled with 11 data points. Applying the method of deconvolution by solving linear equations, in each TMT channel for each peptide the deconvoluted TMT abundance value gives the true TMT abundance value as shown by the plots in FIG. 5B.

In some embodiments, a different approach can be taken to the deconvolution of the reporter ion abundances. Such an approach is suitable, for example, for the embodiments described in which a multiplexed sample is prepared using a set of X mass tags (e.g. X is 2 to 16) and samples labelled with tags 1 to (X−1) in the multiplexed sample are individual peptide samples, typically formed from digestion of individual protein samples, and the $X^{th}$ sample in the multiplexed sample is a pool of the individual samples 1 to (X−1). The individual peptide samples can be digests of single cell proteomes. In the case of single cell proteomes, the $X^{th}$ (pooled) sample can be diluted to an equivalent of N cells (N≤X). For example, in a TMT-10 (i.e. 10-plex set of TMTs) multiplexed sample, 9 of the TMT channels can represent individual samples, such as single cell proteomes, and the $10^{th}$ channel can represent a pooled sample of the other 9 samples, thus reflecting the bulk proteome. The $10^{th}$ TMT channel is diluted to an equivalent of N cells (N≤10). It is assumed that the abundance of an individual reporter ion scales linearly with the abundance of peptide-specific fragment ions. For each peptide, the chromatographic peak (for example the rising slope thereof) of the peptide can be identified from the abundances of the peptide-specific fragment ions in the (DIA) MS2 spectra. Then, the deconvolution of reporter ion abundances for that peptide can be performed by fitting a linear function that correlates the abundance of an individual reporter ion and the abundance of the reporter ion in the $X^{th}$ (e.g. $10^{th}$) sample (i.e. the pooled sample). Thus, a linear function can be fitted to a plot with the "y" axis being the abundance of the individual reporter ion and the "x" axis being the abundance of the reporter ion in the $X^{th}$ tag channel (pooled sample). The slopes of the linear correlations for the respective individual reporter ions represent the relative abundances of the peptide in the respective individual samples. The slope is determined preferably by ignoring the intersection, whereby a substantial part of the signal overlapping with other peptides in the same RT interval is removed. Thus, deconvoluting the abundances of the reporter ions can comprise, within an elution (retention) time for each peptide, which is based on the determined abundances of the peptides, fitting a linear function that correlates the abundance of an individual reporter ion and the abundance of a reporter ion of the pooled sample. This approach to the deconvolution of the reporter ion abundances is simpler, i.e. less mathematically complex, than using the system of linear of equations and matrices but is less accurate, particularly for lower abundance peptides. However, it can still be suitable for many single cell proteomics (SCP) purposes where the peptide abundances deconvoluted from the reporter ions are accurate enough to be used for cell subgroup differentiation.

The disclosure enables the relative abundances of individual peptides in the individual peptide-containing samples to be determined from the reporter ions in the DIA data. From the abundances of the peptides, the abundances of the proteins from which the peptides are derived can be determined. In particular, the peptide or protein abundances are accurate enough for cell subgroup differentiation in single cell proteomics. This allows for peptide or protein variations between samples to be identified.

In particular implementations, the method of the disclosure may further comprise determining a biological state from the determined peptide or protein variations. For example, it may be known that one sample or group of samples is from healthy specimen(s) and the other sample or group of samples is from diseased specimen(s). In another case, it may be known that one sample or group of samples is from male specimen(s) and the other sample or group of samples is from female specimen(s). The determined peptide variations may thus be used to determine a biological state (e.g. healthy or diseased; male or female etc.) for a given sample. The method may also thus comprise assessing a state of disease in view of the determined variations. The method may also comprise finding a marker for a disease (such as a peptide or protein that varies with disease state).

It can be seen from the foregoing that embodiments of the method of mass spectrometry for analysing samples of biomolecules according to the disclosure are a method of deconvoluting mass spectrometry data of mass tags, i.e. reporter ions, in (data-independent acquisition of) mass spectra from multiplexed samples.

According to the disclosure, a mass spectrometer can be used that is under the control of a controller, wherein the controller is configured such that the mass spectrometer is operable to perform the steps of the method according to the present disclosure. The mass spectrometer can comprise: an ionization source for producing precursor ions of the biomolecules provided by a chromatographic device; a mass selector for selecting a mass range of the precursor ions; a fragmentation device for fragmenting precursor ions selected by the mass selector to produce fragment ions; a mass analyser for performing mass analysis of the precursor and fragment ions; and a controller configured to cause the mass spectrometer to perform the method of mass spectrometry according to the method of the disclosure. The controller preferably comprises a computer. A computer program is then preferably provided that, when executed by one or more processors of the computer, causes the one or more processors to carry out the method according to the disclosure, generally by controlling the mass spectrometer to perform the method of mass spectrometry according to the disclosure herein. The computer program may be stored on a computer-readable medium for execution by the processors, for example stored on a flash drive, hard disk drive etc.

Any suitable type of mass spectrometer can be used accordingly to the present disclosure, but preferably a mass spectrometer capable of high-resolution mass spectrometry and accurate mass measurement is used. With high resolution mass spectrometry, exact masses of the biomolecules and their fragments can be measured. Any mass spectrometer capable of mass analysis by DDA and DIA with LC-MS can be used. Preferred examples include mass spectrometers comprising any of the following types of mass analyser: an orbital electrostatic trap mass analyser (e.g. an Orbitrap™ mass analyser from Thermo Scientific), a time-of-flight (TOF) mass analyser, preferably a multiple-reflection TOF (MR-TOF), a Fourier transform mass analyser (FT-MS), for example an FT-ICR mass analyser, an ion trap analyser, etc. The mass spectrometer generally comprises a mass selector, for example a quadrupole mass filter, to enable MS2 analysis of selected ions. The mass spectrometer may employ any suitable type of ion source, especially one compatible with liquid chromatography, such as, for example, electrospray ionization (ESI), including nanospray ionization, etc.

Figure 6:
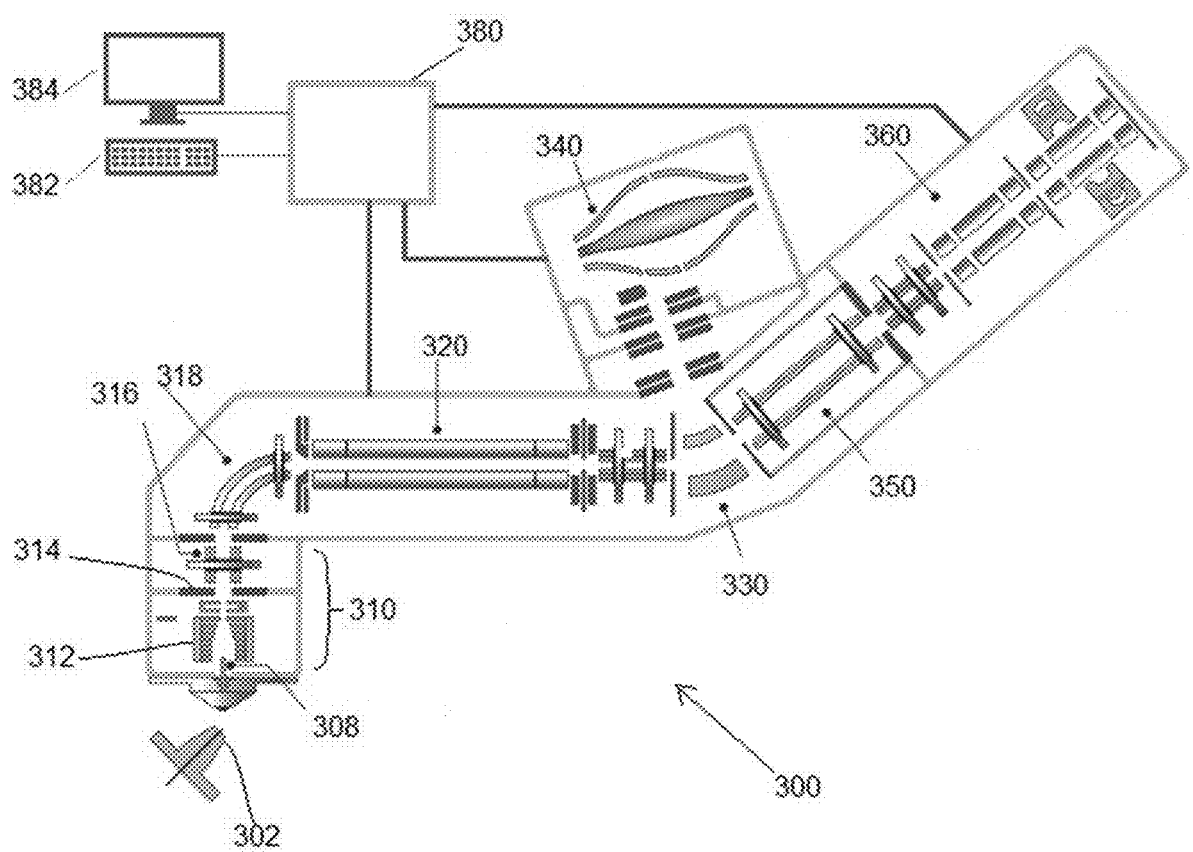
FIG. 6 shows a schematic diagram of a mass spectrometer, which is suitable for performing the method of the disclosure.

A schematic diagram of the layout of the Orbitrap™ Fusion™ Lumos™ Tribrid™ mass spectrometer (Thermo Fisher Scientific™), which is suitable for performing the method of the disclosure, is shown in FIG. 6. It is noted that the Orbitrap™ Fusion™ Lumos™ or other tribrid mass spectrometer is not essential to the present disclosure and other mass spectrometers may be used, e.g. a Q Exactive™ Orbitrap™ series or Orbitrap™ Exploris™ Series mass spectrometer (Thermo Fisher Scientific™), or a Q-TOF type mass spectrometer. The mass spectrometer 300 comprises an atmospheric pressure ionization (API) source 302 that forms gas phase sample ions (precursor ions) from biomolecules that are contained in solution. The API in the example below is an electrospray ionisation (ESI) source. In general precursor ions can be generated from peptides by any of the following ion sources: electrospray ionisation (ESI), atmospheric pressure chemical ionisation (APCI), atmospheric pressure photoionisation (APPI), atmospheric pressure gas chromatography (APGC) with glow discharge, AP-MALDI, laser desorption (LD), inlet ionization, DESI, laser ablation electrospray ionisation (LAESI), inductively coupled plasma (ICP), laser ablation inductively coupled plasma (LA-ICP), etc. Any of these ion sources can be interfaced to any of the following sample separation device upstream of the ion source: liquid chromatography (LC), ion chromatography (IC), gas chromatography (GC), capillary zone electrophoresis (CZE), two dimensional GC (GC×GC), two dimensional LC (LC×LC), etc, which are all herein termed chromatographic devices. The ionization source 302 produces precursor ions of the biomolecules provided by a chromatographic device The mass spectrometer 300 further comprises: source injection optics 310 through which precursor ions pass. The source injection optics 310 comprises: a capillary transfer tube 308, an electrodynamic ion funnel 312; a lens 314; an injection flatapole 316 and a bent ion guide 318. A quadrupole mass selective device (mass filter) 320 allows selecting a mass range of the precursor ions in a variable mass isolation window that is narrower than the full mass range of precursor ions from the ionisation source. The quadrupole mass selective device 320 can also be operated to transmit a full mass range of precursors ions, e.g. for a survey scan (in MS1 mode). A curved linear ion trap (C-trap) 330 configured to apply axial trapping voltages accumulates ions for injection into the Orbitrap™ mass analyser 340 for recording mass spectra, for example high resolution MS1 survey scans. For MS2 mode, ions that have been mass selected by the quadrupole mass selective device 320 can be transmitted through the C-trap 330 by modifying the axial trapping voltages to permit transmission into the gas-filled multipole collision cell 350, which fragments ions according to collisional dissociation (CD). Other modes of ion dissociation are possible with the spectrometer, such as electron transfer dissociation (ETD). In a first mode, the fragmented ions are analysed in the ion trap mass analyser 360. The ion trap mass analyser 360 can be operated in parallel to the Orbitrap mass analyser 340. Accordingly, MS2 spectra can be acquired using the ion trap mass analyser 360 simultaneously with an MS1 spectrum being acquired in the Orbitrap mass analyser. In alternative operation, fragmented ions can be returned to the C-trap 330 and analysed using the Orbitrap mass analyser 340. The components of the mass spectrometer are operated by a controller configured to cause the mass spectrometer 300 to perform the method of mass spectrometry according to the method of the disclosure. The controller comprises a computer 380 having at least one input device such as a mouse and/or keyboard 382 and at least one output device such as a video display 384.

Numerous features or steps can be carried out using the computer. In particular, numerous steps may be realised by operating dedicated data processing software installed in the computer. In particular, the following steps may be carried out using the computer: forming the spectral library; matching peaks in acquired mass spectra to peaks in the spectral library to find spectra matches; determining abundances from acquired spectra; and deconvoluting the abundances of the reporter ions. The computer accordingly preferably comprises a library-forming unit configured to form the spectral library; a matching unit configured to match peaks in acquired mass spectra to peaks in the spectral library to find spectra matches; an abundance unit configured to determine abundances from acquired spectra; and a deconvolution unit configured to deconvolute the abundances of the reporter ions. Each of the library-forming unit, matching unit, abundance unit and deconvolution unit may be provided in the form of program modules of the data processing software.

In embodiments, the computer comprises: a storage medium, a memory, a processor, one or more interfaces, such as a user output interface, a user input interface and a network interface, which are linked together, e.g. over one or more communication buses.

The storage medium may be any form of non-volatile data storage device such as one or more of a hard disk drive, a magnetic disc, an optical disc, a ROM, etc. The storage medium may store one or more computer programs, including a program according to the disclosure.

The memory may be any random access memory (storage unit or volatile storage medium) suitable for storing data and/or computer programs.

The processor may be any data processing unit suitable for executing one or more computer programs (such as those stored on the storage medium and/or in the memory), some of which may include one or more computer programs according to embodiments of the disclosure or computer programs that, when executed by the processor, cause the processor to carry out a method according to an embodiment of the disclosure. The processor may comprise a single data processing unit or multiple data processing units operating in parallel, separately or in co-operation with each other. The processor, in carrying out data processing operations for embodiments of the disclosure, may store data to and/or read data from the storage medium and/or the memory.

An interface may be provided that is any unit for providing an interface between the computer and a device external to, or removable from, the computer. The external device may be a data storage device, for example, one or more of an optical disc, a magnetic disc, a solid-state-storage device, etc. The interface may therefore access data from, or provide data to, or interface with, the external device in accordance with one or more commands that it receives from the processor.

A user input interface may be arranged to receive input from a user, or operator. The user may provide this input via one or more input devices 382 of the system, such as a mouse (or other pointing device) and/or a keyboard, that are connected to, or in communication with, the user input interface. However, it will be appreciated that the user may provide input to the computer via one or more additional or alternative input devices (such as a touch screen). The computer may store the input received from the input devices via the user input interface in the memory for the processor to subsequently access and process, or may pass it straight to the processor, so that the processor can respond to the user input accordingly.

A user output interface may be arranged to provide a graphical/visual output to a user, or operator via an output device. As such, the processor may be arranged to instruct the user output interface to form an image/video signal representing a desired graphical output, and to provide this signal to a video display unit (VDU) 384 such as a monitor (or screen or display unit) that is connected to the user output interface.

A network interface may be arranged to provide functionality for the computer to download data from and/or upload data to one or more data communication networks.

It will be appreciated that the architecture of the computer system described above is merely exemplary and that other computer systems with different architectures (for example with fewer components or with additional and/or alternative components may be used. As examples, the computer could comprise one or more of: a personal computer; a server computer; a laptop; etc.

EXAMPLES

The method of the present disclosure was performed on real samples containing a mixture of standard proteins with some other proteins spiked in at known proportions. The samples contained 15 proteins: 11 of them with the same abundance in all samples and 4 spiked-in with different abundances in the different samples. The samples were digested, labeled with TMT10, multiplexed and analysed by LC-MS/MS. Five conditions/treatments were thereby generated with the different spike-in levels. Each of them was labeled with 2 TMT channels. The spiked-in levels were: 1:4, 1:2, 1:1, 2:1 and 4:1, where the 1:1 is the control.

The multiplexed samples were loaded on a trap column (Acclaim™ PepMap 100C18, 100 μm×2 cm) and separated on a 50 cm long C18 Easy-spray™ column connected to a nanoflow Dionex™ UltiMate™ 3000 UHPLC system (Thermo Fischer Scientific™). Chromatographic separation was performed using an increasing gradient from 4% to 28% (B: 98% ACN, 0.1% FA, 2% $H_2O$) at a flow rate of 300 nL/min over 50 min, followed by a 15 min washout.

An Orbitrap™ Fusion™ Lumos™ Tribrid™ mass spectrometer (Thermo Fischer Scientific™) operating in positive polarity was used for data collection. A DDA analysis was run as control. For DDA analysis, the cycle time was 3 sec and consisted of one full scan with a resolution of 120,000 (at 200 Th) covering the range from 415 to 885 Th, automatic gain control (AGC) was set to $1*10^6$ with a maximum injection time of 50 ms. Triggered MS/MS scans were recorded with a resolution of 60,000, maximum injection time of 118 ms, isolation window of 1.7 Th. Only peptides with a charge from 2+ to 6+ were selected, dynamic exclusion was set to 45 sec. A DIA cycle consisted of one full scan (MS1) with a resolution of 60,000 (at 200 Th) covering a range from 415 to 885 Th, automatic gain control (AGC) set to $1*10^6$ with a maximum injection time of 50 ms, followed by 23 DIA scans of 10 Th each covering a window with their center between 420 and 640 Th. The DIA MS/MS scans were recorded with a resolution of 60,000 (at 200 Th), default charge was set to 3 and with an NCE of 35, scanning a range of 110-1500 Th. All spectra were acquired in profile mode using the Orbitrap™ spectrometer. For converting the raw files to mzML format and centroiding, the MSConvert tool from ProteoWizard was used. Further analysis was performed in R software.

For checking the chromatographic stability between the DIA and the DDA runs, MS1 features extracted by the Dinosaur tool (Teleman et al; *J. Proteome Res.* 15, 2143-2151 (2016)) were compared and retention time aligned by applying a linear correlation model. For DIA and DDA files, TMT reporter ions were extracted as the highest intense peak in a ±0.003 Th window around the expected monoisotopic report mass.

After reading the DDA MS/MS data in R, all unspecific fragments were removed. This included TMT report ions, y1 precursor fragments belonging to R or K, remaining precursor ions, and complementary TMT ions. The spectra were deisotoped applying the algorithm published by Yuan et al (*Adv. Bioinformatics* 2011, (2011).). The remaining fragments were binned into 40 groups with equal m/z spread (m/z range from 320 to 1500), the fragment ion with the highest intensity per bin was determined and the 15 most intense ones of them were kept, as they are most likely to be precursor specific. This resulted in the same number of 'precursor specific fragments' of both identifiable and unidentifiable spectra, required for unbiased downstream analysis. Peptide identification was performed with MaxQuant. Precursor specific fragment ions from the acquired DDA MS2 scans (including unidentified ones) were extracted to form the spectral library. In addition to the 15 proteins known in the samples, MaxQuant also found a few hundred contaminant proteins at low abundances.

To remove duplicated spectral library entries, all spectra (in a 2 min retention time window and with a precursor m/z difference of $10^4$ ppm) were compared to each other. If two spectra are matching with a 'Hyperscore' surpassing a certain cutoff, the more intense one (based on precursor intensity) was kept. The 'Hyperscore' used is described in Searle et al (*Nat. Commun.* 9, 1-12 (2018)). Essentially, the log 10 of the dot product is multiplied by the factorial of matching ions between the library and the DIA spectra.

Matching of the DIA MS/MS (MS2) events to library spectra was then performed. Based on the corrected retention time, each library spectra was matched in a 3 min window against the DIA spectra. Fragment ions were matched with a 10 ppm tolerance; if multiple fragment ions in the DIA spectra were identified, the one with the lowest mass error was considered. In order to assess the probability of a true match, for each library spectra a series of scores was calculated at each time point, which included a 'Hyperscore', the sum of all fragment ions (sum-intensity), as well as the number of matched fragment ions. For further processing, all spectra matches with a maximal Hyperscore less than 2 and with less than 3 matched fragment ions were removed.

Transition refinement was done in the following way. First, the rolling median over 3 windows was calculated based on the following formula: 'Hyperscore'$^2$*log 10(sum-intensity). The DIA spectra with the highest score was considered to be the apex and fragment ions ±20 DIA scans were considered for the following steps. Second, a Gaussian model was fitted for each fragment ion through these points, and fragments with an $R^2<0.85$ were removed. Third, the median intensity of all remaining fragment ions was calculated, and each fragment ion intensity was correlated against this median. Fragment ions with a correlation >0.9 were considered to be quantitative. These fragment ion intensities were summed up in order to determine total precursor peptide abundance and the elution boundaries were determined based on the DIA window before the rolling median over 3 windows of 'Hyperscore'*log 10(sum-intensity) drops below 5% compared to the apex one.

In order to deconvolute the chimeric TMT abundances in the DIA spectra, a system of linear equations as described above was solved, for which two matrices were constructed. The first matrix contains each TMT reporter ion intensity as a column and each spectra retention time as a row (extracted in the preprocessing steps). The second matrix contains each precursor intensity as a column and each spectra retention time as a row (extracted as described before). For deconvoluting the chimeric TMT intensities, the Stark-Parker implementation of bounded-variable least squares algorithm was used (Stark, P. B. & Parker, R. L. *Bounded-Variable Least-Squares: an Algorithm and Application*). The boundaries were set at 0 (in case a precursor is not labeled and likely a contaminant) and infinity for lower and upper boundary, respectively.

Figure 7:
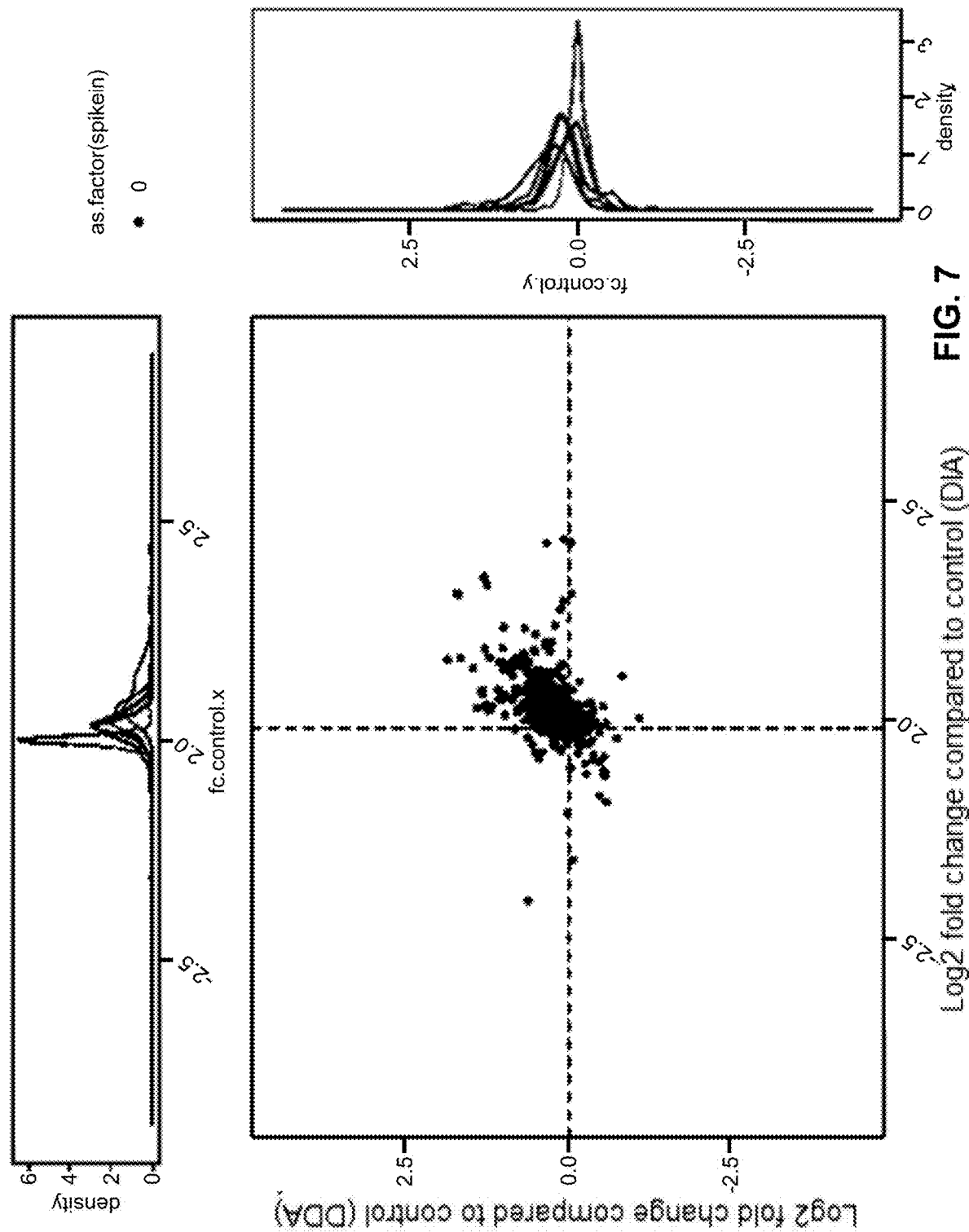
FIG. 7 shows results of TMT deconvolution for the quantification of known background precursors.

Results of the deconvolution are illustrated in FIG. 7 for the quantification of the known background precursors, i.e. those derived from the 11 proteins that were added as background in the same quantity. Their abundance should be constant across the 5 conditions. The central scatter plot shows the log 2 fold change compared to control (DDA) plotted against log 2 fold change compared to control (DIA). The upper and right plots are density plots of the fold change (fc) along x and y respectively. Based on the density plots, DIA and DDA based quantification results in a similar quantification pattern. Most fragments do not show any change in abundance for the background precursors.

Figure 8:
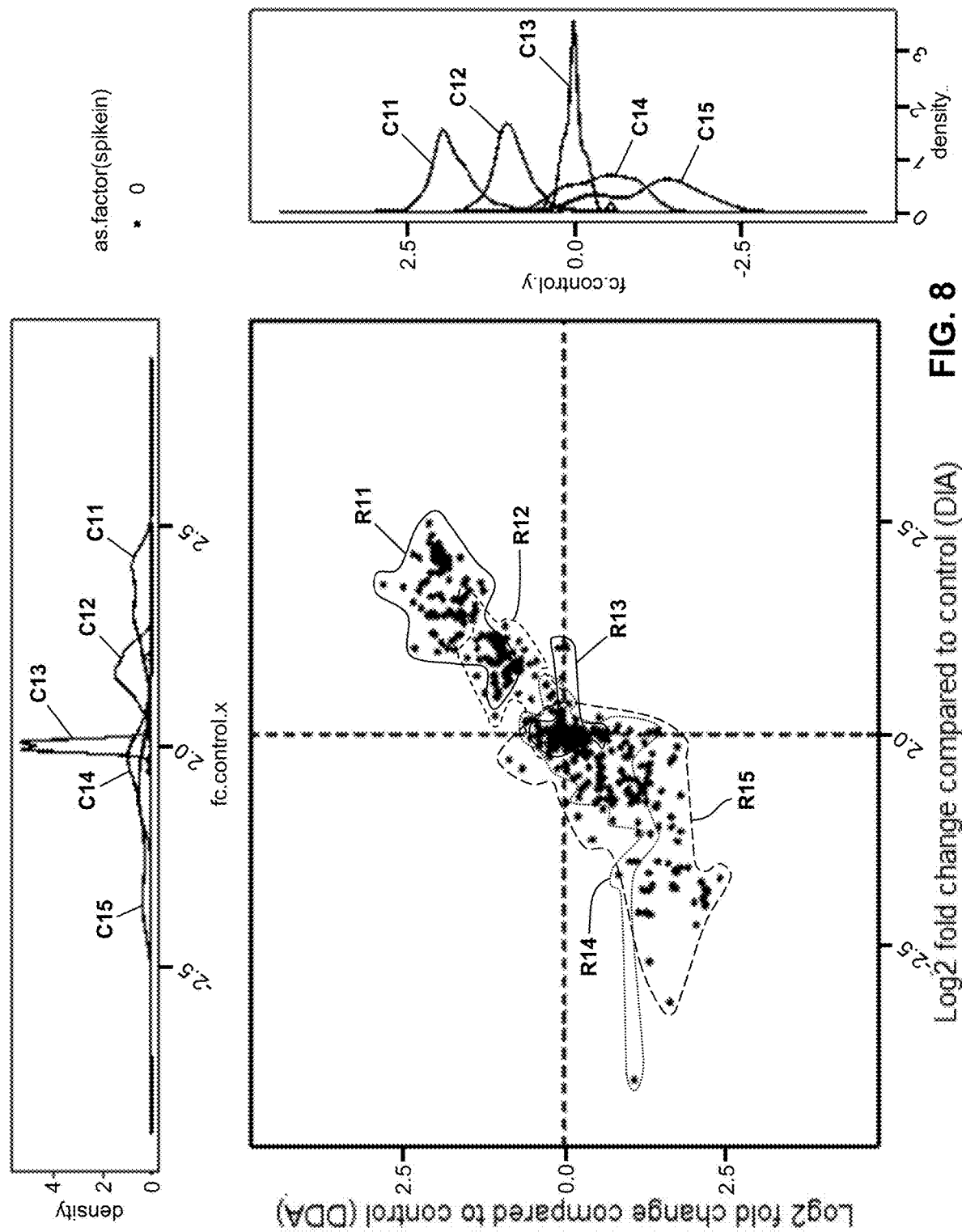
FIG. 8 shows results of TMT deconvolution for the quantification of known 'spiked-in' precursors.
Figure 9:
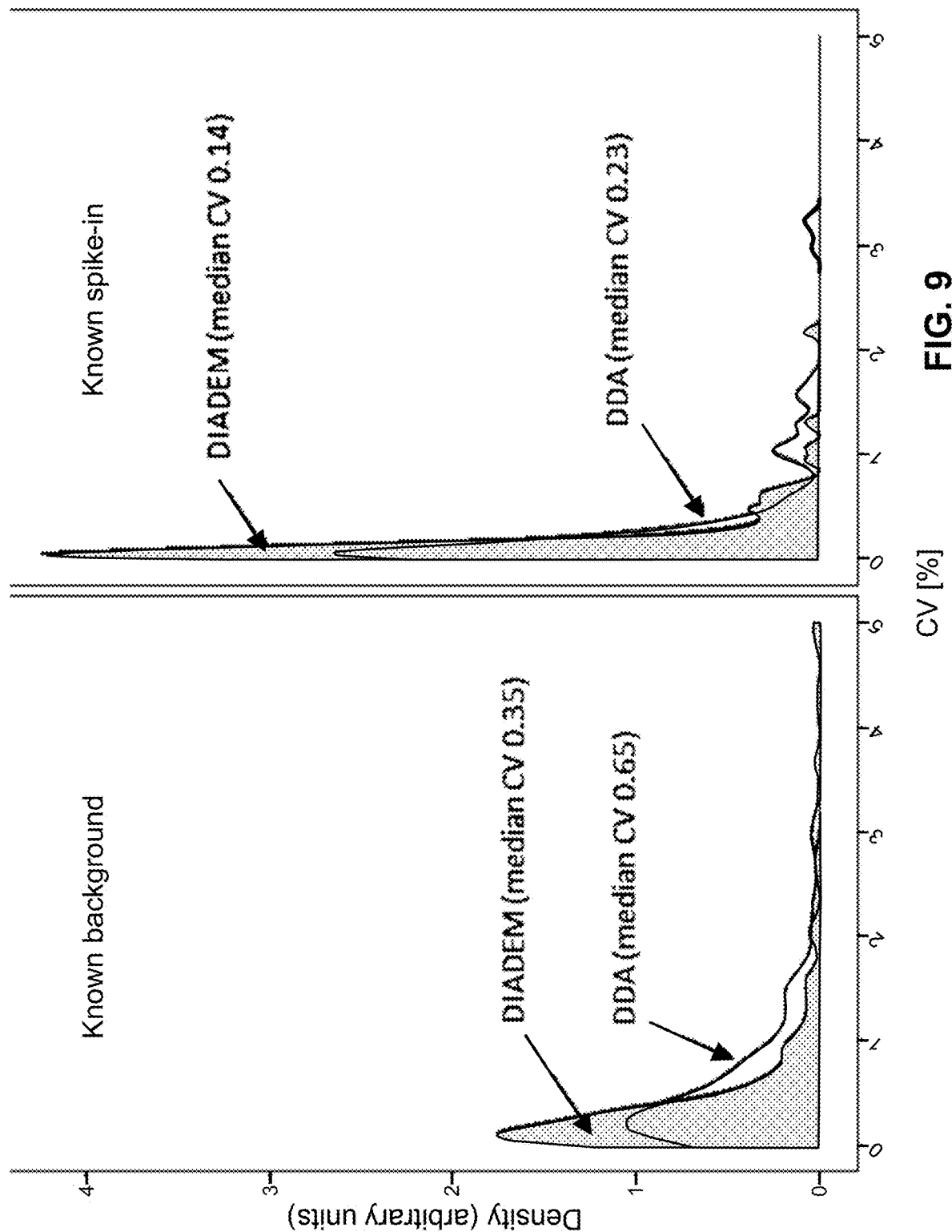
FIG. 9 shows plots of the coefficient of variation (CV) of the fold change for background peptides (on the left) and 'spiked-in' peptides (on the right) from both DDA analysis and DIA with deconvolution using the method of the disclosure.
Figure 10:
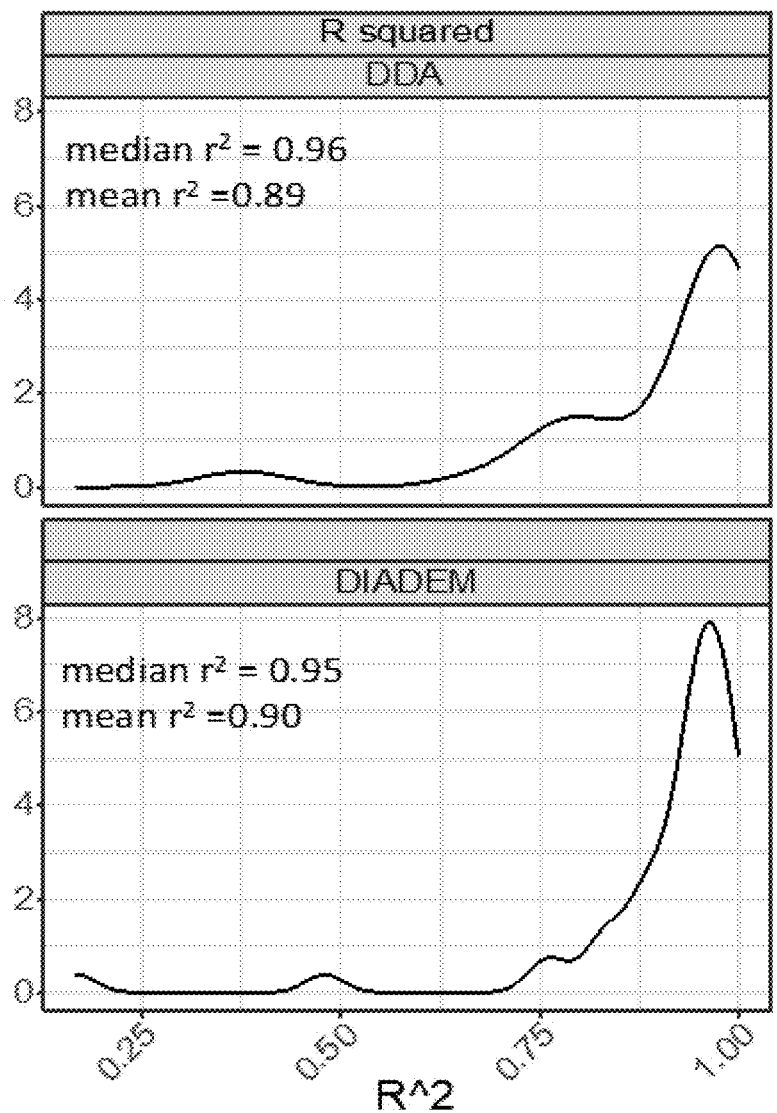
FIG. 10 shows a comparison of measured spiked-in abundances vs known abundance ratios in terms of the correlation coefficient $R^2$ for both DDA (top) and DIA with deconvolution using the method of the disclosure (bottom).

Results of the deconvolution are illustrated in FIG. 8 for the quantification of the known 'spiked-in' precursors, i.e. those derived from the 4 proteins that were added as different quantities in each sample. Their abundance should cluster in 5 distinct clusters, according to the spiked-in ratios. Each one of the graphed cluster regions R11-R15 in FIG. 8 corresponds to a respective one of the peptides; likewise, each of the density curves C11-C15 corresponds to the respective peptide. Based on the scatter plot, the DIA deconvolution algorithm was able to quantify peptides fragments with a comparable accuracy to the DDA based quantitation. Further results are shown in FIG. 9, which shows plots of the coefficient of variation (CV) of the fold change for the peptides from the 15 proteins (2 replicates) from the DDA analysis and from the DIA analysis using the method of the present disclosure, labelled as DIADEM (Data Independent Acquisition with DEconvolution of Multiplexing). The CV plot on the left is for the known background peptides and the CV plot on the right is for the spiked-in peptides. The quantification using the method of the present disclosure gives lower CVs than the DDA analysis. FIG. 10 shows a comparison of measured spiked-in abundances vs known abundance ratios. All abundances of spiked-in peptides were fitted with a linear regression (y=ax+b) with known relative abundances ("ground truth"). The correlation coefficient R was calculated for each peptide. The median and average values of $R^2$ (R squared) for the method of the present disclosure and DDA are nearly identical.

The terms mass and m/z are used herein interchangeably and accordingly a reference to one is to be construed as including a reference to the other. Similarly, the terms scan (or scans) and spectrum (or spectra) are used herein interchangeably. Likewise, the terms intensity (or intensities) and abundance (or abundances) in the context of mass spectra are used interchangeably.

The order of performing steps described in this disclosure is not strictly limited to that described, such that steps may be performed in another order unless the context explicitly or implicitly indicates otherwise. That is, to the extent that a method or process does not rely on the particular order of steps set forth herein, the method or process is not e limited to the particular sequence of steps described.

As used herein, including in the claims, unless the context indicates otherwise, singular forms of the terms herein are to be construed as including the plural form and vice versa. For instance, unless the context indicates otherwise, a singular reference herein, such as "a" or "an" means "one or more".

Throughout the description and claims of this specification, the words "comprise", "including", "having" and "contain" and variations of the words, for example "comprising" and "comprises" etc., mean "including but not limited to" and are not intended to (and do not) exclude other components.

It will be appreciated that variations to the foregoing embodiments of the disclosure can be made while still falling within the scope of the disclosure as defined by the claims. Each feature disclosed in this specification, unless stated otherwise, may be replaced by alternative features serving the same, equivalent or similar purpose. Thus, unless stated otherwise, each feature disclosed is one example only of a generic series of equivalent or similar features.

The use of any and all examples, or exemplary language ("for instance", "such as", "for example" and like language) provided herein, is intended merely to better illustrate the disclosure and does not indicate a limitation on the scope of the disclosure unless otherwise claimed. No language in the specification should be construed as indicating any non-claimed element as essential to the practice of the disclosure.

The invention claimed is:

1. A method of mass spectrometry for analysing samples of biomolecules, comprising:
   providing a multiplexed sample comprising a mixture of biomolecule-containing samples, wherein the biomolecule-containing samples are respectively tagged with mass tags having respective reporter ions;
   acquiring MS2 spectra by data-dependent acquisition (DDA) of the multiplexed sample or another mass tagged mixture of the biomolecule-containing samples as it elutes from a liquid chromatographic device;
   acquiring MS2 spectra by data-independent acquisition (DIA) of the multiplexed sample as it elutes from the liquid chromatographic device;
   forming a spectral library from the MS2 spectra acquired by DDA comprising a plurality of MS2 spectra representing a plurality of mass-tagged molecular ions of biomolecules and their fragment ions and the retention times of the biomolecules;

matching peaks of fragment ions in the MS2 spectra acquired by DIA to peaks of fragment ions in the MS2 spectra of the spectral library to find matched biomolecules;

determining a total abundance for all mass tags for each matched biomolecule from the MS2 spectra acquired by DIA at each of a plurality of retention times;

determining abundances of respective reporter ions derived from the mass tags from the MS2 spectra acquired by DIA at the plurality of retention times; and deconvoluting relative abundances of the biomolecules in each respectively tagged biomolecule-containing sample based on the determined abundances of the respective reporter ions and the determined total abundances of the matched biomolecules at corresponding retention times over the plurality of retention times, wherein the deconvoluting comprises using a set of linear equations, wherein each linear equation relates to a different one of the plurality of retention times.

2. The method of mass spectrometry according to claim 1, wherein the biomolecules are peptides.

3. The method of mass spectrometry according to claim 2, wherein the peptides are produced by digesting proteins.

4. The method of mass spectrometry according to claim 2, wherein the peptides are produced by digesting single cell proteomes.

5. The method of mass spectrometry according to claim 1, wherein the mass tags are tandem mass tags (TMTs).

6. The method of mass spectrometry according to claim 1, wherein the spectral library comprises MS2 spectra for both identified and unidentified biomolecules.

7. The method of mass spectrometry according to claim 6, wherein the MS2 spectra in the spectral library for identified biomolecules are obtained by finding peaks in MS1 spectra acquired by the data-dependent acquisition (DDA).

8. The method of mass spectrometry according to claim 7, wherein correlating fragment ions that are not supported by the identified structures of the biomolecules are used to represent unidentified biomolecules in the spectral library.

9. The method of mass spectrometry according to claim 7, wherein finding the peaks in MS1 spectra comprises identifying isotopic clusters in the MS1 spectra that are expected to belong to biomolecules, finding peaks of fragment ions in the MS2 spectra acquired by DDA that correlate with the peaks in the MS1 spectra, and identifying structures of the biomolecules based on the peaks in MS1 and the correlating peaks of fragment ions.

10. The method of mass spectrometry according to claim 9, wherein the MS2 spectra in the spectral library for the identified biomolecules comprise only correlating peaks of fragment ions that are supported by the identified structures.

11. The method of mass spectrometry according to claim 6, wherein the unidentified biomolecules comprise dark proteome peptides.

12. The method of mass spectrometry according to claim 1, wherein, in the matching, mass spectra in the spectral library are each matched against the MS2 spectra acquired by DIA in a retention time window around the retention time of the library mass spectra.

13. The method of mass spectrometry according to claim 12, further comprising calculating for each MS2 spectrum in the spectral library a series of probability scores at each time point in the retention time window and removing a number of spectra from the matching based on the series of probability scores.

14. The method of mass spectrometry according to claim 13, wherein the series of probability scores comprises a spectra matching score, a sum-intensity of all matched fragment ions and/or a number of matched fragment ions.

15. The method of mass spectrometry according to claim 1, wherein determining the total abundance for all mass tags for each matched biomolecule comprises summing intensities of peaks of fragment ions and molecular ions of the matched biomolecule in MS2 spectra acquired by DIA.

16. The method of mass spectrometry according to claim 15, wherein an apex of the elution of each biomolecule is determined and a predetermined number of the MS2 spectra acquired by DIA either side of the apex are used to determine the retention time interval.

17. The method of mass spectrometry according to claim 15, further comprising fitting a peak shape model for the intensity of each matched fragment ion through the time points in the retention time interval, wherein fragment ions with a correlation below a threshold for the model are removed.

18. The method of mass spectrometry according to claim 15, further comprising calculating a median intensity of all matched peaks of fragment ions in the MS2 spectra acquired by DIA, and correlating each fragment ion intensity against the median, wherein fragment ions not having a correlation above a threshold are removed.

19. The method of mass spectrometry according to claim 15, wherein determining the total abundance for all mass tags for each matched biomolecule comprises calculating a sum of intensities of matched peaks in the MS2 spectra acquired by DIA in a retention time interval.

20. The method of mass spectrometry according to claim 1, wherein each linear equation relates the determined abundances of the respective reporter ions to a linear combination of the abundances of the biomolecules in each of the biomolecule-containing samples at a respective retention time, wherein the abundance of each biomolecule in each of the samples is expressed as the determined total abundance of the biomolecule multiplied by the relative abundance of the biomolecule in the sample.

21. The method of mass spectrometry according to claim 1, wherein deconvoluting the abundances of the reporter ions comprises solving matrices, wherein a first matrix (M1) comprises the determined abundances of the respective reporter ions as columns with the retention times corresponding to the rows, a second matrix (M2) comprises the determined total abundances of the matched biomolecules as columns with the retention times corresponding to the rows, a third matrix (M3) comprises the relative abundances of the biomolecules in each biomolecules-containing sample and M1=M2*M3.

22. The method of mass spectrometry according to claim 1, wherein one of the biomolecule-containing samples is a pooled sample of the other samples and deconvoluting the abundances of the reporter ions comprises, within an elution time for each biomolecule based on the determined abundances of the biomolecules, fitting a linear function that correlates the abundance of an individual reporter ion and the abundance of a reporter ion of the pooled sample.

23. A mass spectrometer for analysing samples of biomolecules, comprising:

an ionization source for producing precursor ions of the biomolecules provided by a chromatographic device;

a mass selector for selecting a mass range of the precursor ions;

a fragmentation device for fragmenting precursor ions selected by the mass selector to produce fragment ions;

a mass analyser for performing mass analysis of the precursor and fragment ions; and a controller configured to cause the mass spectrometer to:
  acquire MS2 spectra by data-dependent acquisition (DDA) of either a multiplexed sample comprising a mixture of biomolecule-containing samples as it elutes from a liquid chromatographic device or another mixture of the biomolecule-containing samples as it elutes from the liquid chromatographic device, wherein the biomolecule-containing samples are respectively tagged with mass tags having respective reporter ions;
  acquire MS2 spectra by data-independent acquisition (DIA) of the multiplexed sample as it elutes from the liquid chromatographic device;
  form a spectral library from the MS2 spectra acquired by DDA comprising a plurality of MS2 spectra representing a plurality of mass-tagged molecular ions of biomolecules and their fragment ions and the retention times of the biomolecules;
  match peaks of fragment ions in the MS2 spectra acquired by DIA to peaks of fragment ions in the MS2 spectra of the spectral library to find matched biomolecules;
  determine a total abundance for all mass tags for each matched biomolecule from the MS2 spectra acquired by DIA at each of a plurality of retention times;
  determine abundances of respective reporter ions derived from the mass tags from the MS2 spectra acquired by DIA at the plurality of retention times; and
  deconvolute relative abundances of the biomolecules in each respectively tagged biomolecule-containing sample based on the determined abundances of the respective reporter ions and the determined total abundances of the matched biomolecules at corresponding retention times over the plurality of retention times,
  wherein the deconvoluting comprises using a set of linear equations, wherein each linear equation relates to a different one of the plurality of retention times.

* * * * *